(12) United States Patent
Kumazaki et al.

(10) Patent No.: US 7,914,478 B2
(45) Date of Patent: Mar. 29, 2011

(54) INTRAPELVIC PERFUSION THERAPY WITH CANCER THERAPEUTIC AGENT AND APPARATUS FOR INTRAPELVIC PERFUSION WITH CANCER THERAPEUTIC AGENT

(76) Inventors: Tatsuo Kumazaki, Tokyo (JP); Satoru Murata, Tokyo (JP)

( * ) Notice: Subject to any disclaimer, the term of this patent is extended or adjusted under 35 U.S.C. 154(b) by 1971 days.

(21) Appl. No.: 10/106,790

(22) Filed: Mar. 27, 2002

(65) Prior Publication Data

US 2003/0153871 A1    Aug. 14, 2003

(51) Int. Cl.
*A61M 37/00* (2006.01)
*A61M 29/00* (2006.01)
(52) U.S. Cl. .............. 604/6.11; 604/6.16; 604/96.01
(58) Field of Classification Search .......... 604/4.01, 604/5.01, 5.04, 6.09, 6.11, 6.14, 500, 507–88, 604/96.01, 264, 509; 210/645–646
See application file for complete search history.

(56) References Cited

U.S. PATENT DOCUMENTS

| | | | | |
|---|---|---|---|---|
| 5,069,662 | A | * | 12/1991 | Bodden ................ 604/5.01 |
| 5,817,046 | A | * | 10/1998 | Glickman ................ 604/5.04 |
| 6,699,231 | B1 | * | 3/2004 | Sterman et al. ................ 604/509 |

OTHER PUBLICATIONS

Regional perfusion of the pelvis: consideration of the "leakage" problem. Lawrence et al. Surgery, vol. 50, No. 1. pp. 248-259. Jul. 1961.
Treatment of malignant pelvic tumors by extracorporeal perfusion with chemotherapeutic agents. Austen et al. Journal of Medicine, vol. 261, No. 21. Nov. 19, 1959.
Regional Chemotherapy for Cancer: Experiences with 116 Perfusions. Stehlin et al. Annals of Surgery, vol. 151, No. 4. pp. 605-619. Apr. 1960.
Isolated Pelvic Perfusion for Unresectable Cancer Using a Balloon Occlusion Technique. Turk et al. Arch Surg, vol. 128, pp. 533-539. May 1993.
Pharmacokinetic model and the clinical pharmacology of cis-platinum, fluorouracil and mitomycin-C in isolated pelvic perfusion. Wanebo et al. Cancer Chemother Pharmacol., 43: 427-434. 1999.
Preoperative Therapy for Advanced Pelvic Malignancy by Isolated Pelvic Perfusion with the Balloon-Occlusion Technique. Wanebo et al. Annals of Surgical Oncology, 3(3):295-303, 1996.
Chemotherapy of Cancer: Regional Perfusion Utilizing an Extracorporeal Circuit. Creech, Jr. et al. Annals of Surgery, vol. 148, No. 4. pp. 616-632. Oct. 1958.

* cited by examiner

*Primary Examiner* — Leslie R Deak
(74) *Attorney, Agent, or Firm* — Bacon & Thomas, PLLC

(57) ABSTRACT

An intra pelvic cancer therapeutic agent perfusion apparatus and method for administering a cancer therapeutic agent to and recovering same from a cancer tissue site within the pelvis. The tip of a first sheath is percutaneously inserted into the femoral artery and the tip of a second sheath is inserted into the femoral vein. A first balloon catheter is inserted into the aorta through the femoral artery and a second balloon catheter is inserted into the vena cava through the femoral vein. The first balloon catheter is used to block the blood flow and the second balloon is inflated to form an intravenous closed region between the site of insertion in the vena cava and a lower limb side venous site. A body fluid containing a cancer therapeutic agent is administered to the intra arterial closed region through the first sheath and is removed therefrom through the second sheath.

16 Claims, 11 Drawing Sheets

INTRAPELVIC PERFUSION THERAPY WITH CANCER THERAPEUTIC AGENT AND APPARATUS FOR INTRAPELVIC PERFUSION WITH CANCER THERAPEUTIC AGENT

BACKGROUND OF THE INVENTION

1. Technical Field of the Invention

The present invention relates to a method of cancer treatment by intrapelvic perfusion with a cancer therapeutic agent, comprising administering at least one of an anticancer agent, a radioisotope, a gene for gene therapy, a DNA molecule for gene therapy, RNA molecule for gene therapy and a cell for gene therapy to and recovering from an advanced cancer tissue site within the pelvis and to an apparatus for intrapelvic perfusion with a cancer therapeutic agent.

2. Prior Art

In the art, upon detection or diagnosis of early cancer in the bladder, uterus, lymph node or other tissues located within the pelvis, surgical procedures have been performed as a reliable method of short-term treatment thereof.

However, in cases where doubt remains even after surgical treatment as to residual tumor (cancer) tissues, radiation therapy and/or immunotherapy may be given postoperatively in certain instances. Further, in cases where the cancer is in such an advanced stage that no operative procedure can be applied, for example in the advanced metastatic stage, cancer chemotherapy comprising administering an anticancer agent is used in combination with surgical procedures.

In cancer chemotherapy, the technique of anticancer agent perfusion has been employed which comprises extracorporeally circulating an anticancer agent using an extracorporeal blood circulation device or system, as reported by Peter S. Turk, James F. Belliveau, et al. (Archives of Surgery vol. 128, May 1993).

In anticancer agent perfusion therapy, two balloon catheters are indwelled in an aorta and a cava, respectively. They are inflated for blocking the vessels to thereby block the blood flow while the blood flow in the lower limbs is blocked by means of tourniquets. An anticancer agent-containing fluid is fed to the thus-formed closed region and discharged therefrom continuously for 30 to 40 minutes using an extracorporeal blood circulation device.

The above therapeutic method using an anticancer agent has made it possible to erase tumors or prevent them from growing and/or alleviate the symptoms caused by tumors.

In the conventional anticancer agent perfusion therapy, the volume of the anticancer agent-containing fluid fed into the aorta by an extracorporeal blood circulation device and the volume of the blood-containing body fluid discharged through the cava by the same device are equal to each other.

However, among the aorta and cava, those occurring within the pelvis, in particular, have a number of developed collateral routes for blood circulation. Therefore, when the feeding rate and discharge rate are equal to each other, the venous pressure in the pelvic circulation is higher than that in the systemic circulation, as a result, there arises the problem that the anticancer agent-containing fluid may readily leak out through the collateral blood vessels into blood flow routes occurring outside the pelvis, hence into the whole body.

Though the gene therapy for cancer has recently been performed, a therapeutic method of effectively sending a gene, a DNA molecule, a RNA molecule, a cell, and a radioisotope for cancer gene therapy to the tumor has been expected.

SUMMARY OF THE INVENTION

Accordingly, it is an object of the present invention to provide a cancer therapeutic agent perfusion therapy which can be used in the treatment of advanced cancer tissue sites occurring in the bladder, uterus or the like tissue or organ located within the pelvis and by which the therapeutic agent for cancer fed to the cancer tissue sites can be prevented from leaking into blood flow routes occurring outside the pelvis, hence the adverse effects of the therapeutic agent for cancer on the patient can be prevented, as well as a cancer therapeutic agent perfusion apparatus therefor.

It is another object of the present invention to provide a cancer therapeutic agent perfusion therapy which can be used in the treatment of advanced cancer tissue sites occurring in the bladder, uterus or the like tissue or organ located within the pelvis and by which a gene, a DNA molecule, a RNA molecule, a cell, and a radioisotope for cancer gene therapy can be effectively sent to the tumor, as well as a cancer therapeutic agent perfusion apparatus therefor.

The invention is now described referring to typical embodiments defined in the claims.

The cancer therapeutic agent perfusion therapy according to the present invention, which is a cancer therapeutic agent perfusion therapy consisting in administering a cancer therapeutic agent to and recovering the same from a cancer tissue site, comprises the step of percutaneously inserting the tip of a first sheath, which is a tubular body, into the femoral artery and causing the sheath to indwell therein, the step of percutaneously inserting the tip of a second sheath, which is a tubular body, into the femoral vein and causing the sheath to indwell therein, the step of percutaneously inserting a first balloon catheter having an inflatable first balloon at the tip of a flexible tubular body into the aorta through the femoral artery and causing the first balloon to indwell at a predetermined site of the aorta, the step of percutaneously inserting a second balloon catheter having an inflatable second balloon at the tip of a flexible tubular body into the vena cava through the femoral vein and causing the second balloon to indwell at a predetermined site of the cava, the step of blocking the blood flow at a lower limb side arterial site lower than the above predetermined site of the aorta, the step of blocking the blood flow at a lower limb side venous site lower than the above predetermined site of the cava, the step of inflating the first balloon to thereby form an intraarterial closed region between the above predetermined site of the aorta and the above lower limb side arterial site, the step of inflating the second balloon to thereby form an intravenous closed region between the above predetermined site of the cava and the above lower limb side venous site, the step of administering a body fluid containing a cancer therapeutic agent to the intraarterial closed region from the above first sheath, and the step of recovering a larger amount, as compared with the body fluid containing the above cancer therapeutic agent as fed, of a body fluid containing the cancer therapeutic agent from the above intravenous closed region through the second sheath.

Thus, by recovering the cancer therapeutic agent-containing body fluid from the cava in a larger amount than the amount of the cancer therapeutic agent-containing body fluid administered into the aorta so that the rate of discharging cancer therapeutic agent-containing body fluid from the cava may be higher than the rate of cancer therapeutic agent-containing body fluid feeding into the aorta, it becomes possible to make the pressure on the fluid discharge side lower than that on the fluid feeding side in the system connecting the feeding side with the discharge side to thereby prevent the cancer therapeutic agent from leaking into the blood circulation system outside the pelvis while maintaining the effects of the anticancer agent on the cancer tissue or tissues.

In another embodiment of the cancer therapeutic agent perfusion therapy according to the invention, which is a cancer therapeutic agent perfusion therapy consisting in administering a cancer therapeutic agent to and recovering the same from a cancer tissue site, comprises the step of percutaneously inserting a first balloon catheter having a first inflatable balloon at the tip of a flexible tubular body and a first hollow tubular part connecting the rear end portion of the above tubular body with the tip portion thereof, into the aorta through the femoral artery and causing the first balloon to indwell in the aorta at a predetermined site, the step of causing a second balloon catheter having a second inflatable balloon at the tip of a flexible tubular body and a second hollow tubular part connecting the rear end portion of the above tubular body with the tip portion thereof, to indwell in the vena cava at a predetermined site, the step of blocking the blood flow at a lower limb side arterial site lower than the above predetermined site of the aorta, the step of blocking the blood flow at a lower limb side venous site lower than the above predetermined site of the cava, the step of inflating the first balloon to thereby form an intraarterial closed region between the above predetermined site of the aorta and the above lower limb side arterial site, the step of inflating the second balloon to thereby form an intravenous closed region between the above predetermined site of the cava and the above lower limb side venous site, the step of administering a body fluid containing a cancer therapeutic agent to the intraarterial closed region from the above first hollow tubular part, and the step of recovering a larger amount, as compared with the body fluid containing the above the cancer therapeutic agent as fed, of a body fluid containing the cancer therapeutic agent from the above intravenous closed region through the second hollow tubular part.

Since, in the above manner, the first balloon catheter and the second balloon catheter each by itself makes it possible to block the blood flow by inflating the balloon and administer the agent to or recover the same from the body, the number of tools or the like to be percutaneously insert into the body or blood vessels of a patient and indwelled therein can be reduced.

Further, by recovering the cancer therapeutic agent-containing body fluid from the cava in a larger amount than the amount of the cancer therapeutic agent-containing body fluid administered into the aorta so that the rate of discharging cancer therapeutic agent-containing body fluid from the cava may be higher than the rate of cancer therapeutic agent-containing body fluid feeding into the aorta, it becomes possible to make the pressure on the fluid discharge side lower than that on the fluid feeding side in the system connecting the feeding side with the discharge side to thereby prevent the cancer therapeutic agent from leaking into the blood circulation system outside the pelvis while maintaining the effects of the anticancer agent on the cancer tissue or tissues.

In the step of administering the body fluid containing the cancer therapeutic agent and in the step of recovering the body fluid, an extracorporeal blood circulation device is used.

By doing so, it is possible to administer and recover the body fluid containing the cancer therapeutic agent with certainty and to precisely control the amount thereof administered and the amount thereof recovered.

At least one of an anticancer agent, a radioisotope, a gene for gene therapy, a DNA molecule for gene therapy, RNA molecule for gene therapy or a cell for gene therapy can be used as the cancer therapeutic agent.

By this, cancer can intensively be treated.

The cancer therapeutic agent perfusion therapy according to the invention further comprises the step of subjecting the body fluid recovered in the body fluid recovering step to blood cleansing treatment, which includes at least one of hemodialysis, hemofiltration, hemoabsorption and centrifugation and then sending the thus-treated body fluid back into the body.

By this, the cancer therapeutic agent can be removed from the body fluid recovered, and the blood can be sent back again into the body.

In another embodiment of the cancer therapeutic agent perfusion therapy according to the invention, which is a cancer therapeutic agent perfusion therapy consisting in administering a cancer therapeutic agent to and recovering the same from a cancer tissue site, comprises the step of percutaneously inserting the tip of a first sheath, which is a tubular body, into the femoral artery and causing the sheath to indwell therein, the step of percutaneously inserting the tip of a second sheath, which is a tubular body, into the femoral vein and causing the sheath to indwell therein, the step of percutaneously inserting a first balloon catheter having an inflatable first balloon at the tip of a flexible tubular body into the aorta through the femoral artery and causing the first balloon to indwell at a predetermined site of the aorta, the step of percutaneously inserting a second balloon catheter having an inflatable second balloon at the tip of a flexible tubular body into the vena cava through the femoral vein and causing the second balloon to indwell at a predetermined site of the cava, the step of blocking the blood flow at a lower limb side arterial site lower than the above predetermined site of the aorta, the step of blocking the blood flow at a lower limb side venous site lower than the above predetermined site of the cava, the step of inflating the first balloon to thereby form an intraarterial closed region between the above predetermined site of the aorta and the above lower limb side arterial site, the step of inflating the second balloon to thereby form an intravenous closed region between the above predetermined site of the cava and the above lower limb side venous site, the step of administering a body fluid containing a cancer therapeutic agent to the intraarterial closed region from the above first sheath, and the step of recovering a body fluid containing the cancer therapeutic agent from the above intravenous closed region through the second sheath, the step of subjecting the body fluid recovered in the body fluid recovering step to blood cleaning treatment comprising at least one of hemodialysis, hemofiltration, hemoabsorption and centrifugation and sending the thus-treated body fluid back into the body.

In another embodiment of the cancer therapeutic agent perfusion therapy according to the invention, which is a cancer therapeutic agent perfusion therapy consisting in administering a cancer therapeutic agent to and recovering the same from a cancer tissue site, comprises the step of percutaneously inserting a first balloon catheter having a first inflatable balloon at the tip of a flexible tubular body and a first hollow tubular part connecting the rear end portion of the above tubular body with the tip portion thereof, into the aorta through the femoral artery and causing the first balloon to indwell in the aorta at a predetermined site, the step of causing a second balloon catheter having a second inflatable balloon at the tip of a flexible tubular body and a second hollow tubular part connecting the rear end portion of the above tubular body with the tip portion thereof, to indwell in the vena cava at a predetermined site, the step of blocking the blood flow at a lower limb side arterial site lower than the above predetermined site of the aorta, the step of blocking the blood flow at a lower limb side venous site lower than the above predetermined site of the cava, the step of inflating the first balloon to thereby form an intraarterial closed region between the above predetermined site of the aorta and the above lower limb side arterial site, the step of inflating the second balloon to thereby form an intravenous closed region between the above predetermined site of the cava and the above lower limb side venous site, the step of administering a body fluid containing a cancer therapeutic agent to the intraarterial closed region from the above first hollow tubular part, and the step of recovering a body fluid containing the anticancer agent from the above intravenous closed region through the second hollow tubular part, the step of subjecting the body fluid recovered in the body fluid recovering step to blood cleaning treatment comprising at least one of hemodialysis, hemofiltration, hemoabsorption and centrifugation and sending the thus-treated body fluid back into the body.

By this, the cancer therapeutic agent can be removed from the body fluid recovered, and the blood can be sent back again into the body.

In another embodiment of the cancer therapeutic agent perfusion therapy according to the invention, which is a cancer therapeutic agent perfusion therapy consisting in administering a cancer therapeutic agent to and recovering the same from a cancer tissue site occurring within the pelvis, characterized in that it comprises the step of percutaneously inserting the tip of a first sheath, which is a tubular body, into the femoral artery and causing the sheath to indwell therein, the step of percutaneously inserting the tip of a second sheath, which is a tubular body, into the femoral vein and causing the sheath to indwell therein, the step of percutaneously inserting a first balloon catheter having an inflatable first balloon at the tip of a flexible tubular body into the aorta through the femoral artery and causing the first balloon to indwell at a predetermined site of the aorta, the step of percutaneously inserting a second balloon catheter having an inflatable second balloon at the tip of a flexible tubular body into the vena cava through the femoral vein and causing the second balloon to indwell at a predetermined site of the cava, the step of blocking the blood flow at a lower limb side arterial site lower than the above predetermined site of the aorta, the step of blocking the blood flow at a lower limb side venous site lower than the above predetermined site of the cava, the step of inflating the first balloon to thereby form an intraarterial closed region between the above predetermined site of the aorta and the above lower limb side arterial site, the step of inflating the second balloon to thereby form an intravenous closed region between the above predetermined site of the cava and the above lower limb side venous site, the step of administering a body fluid containing a cancer therapeutic agent to the intraarterial closed region from the above first sheath, and the step of recovering a body fluid containing the cancer therapeutic agent from the above intravenous closed region through the second sheath, the above cancer therapeutic agent is at least one agent chosen from the group of an anticancer agent, a radioisotope, a gene for gene therapy, a DNA molecule for gene therapy, RNA molecule for gene therapy and a cell for gene therapy.

In another embodiment of the cancer therapeutic agent perfusion therapy according to the invention, which is a cancer therapeutic agent perfusion therapy consisting in administering a cancer therapeutic agent to and recovering the same from a cancer tissue site occurring within the pelvis, characterized in that it comprises the step of percutaneously inserting a first balloon catheter having a first inflatable balloon at the tip of a flexible tubular body and a first hollow tubular part connecting the rear end portion of the above tubular body with the tip portion thereof, into the aorta through the femoral artery and causing the first balloon to indwell in the aorta at a predetermined site, the step of causing a second balloon catheter having a second inflatable balloon at the tip of a flexible tubular body and a second hollow tubular part connecting the rear end portion of the above tubular body with the tip portion thereof, to indwell in the vena cava at a predetermined site, the step of blocking the blood flow at a lower limb side arterial site lower than the above predetermined site of the aorta, the step of blocking the blood flow at a lower limb side venous site lower than the above predetermined site of the cava, the step of inflating the first balloon to thereby form an intraarterial closed region between the above predetermined site of the aorta and the above lower limb side arterial site, the step of inflating the second balloon to thereby form an intravenous closed region between the above predetermined site of the cava and the above lower limb side venous site, the step of administering a body fluid containing a cancer therapeutic agent to the intraarterial closed region from the above first hollow tubular part, and the step of recovering a body fluid containing the cancer therapeutic agent from the above intravenous closed region through the second hollow tubular part, the above cancer therapeutic agent is at least one agent chosen from the group of an anticancer agent, a radioisotope, a gene for gene therapy, a DNA molecule for gene therapy, RNA molecule for gene therapy and a cell for gene therapy.

The cancer therapeutic agent perfusion apparatus according to the present invention, which is a cancer therapeutic agent perfusion apparatus for administrating a cancer therapeutic agent to and recovering the same from a cancer tissue site, comprises a fluid feeding tube for intracorporeally feeding an cancer therapeutic agent-containing extracorporeal medical fluid and at least one of blood and a body fluid, a fluid discharge tube for discharging the intracorporeal an cancer therapeutic agent-containing fluid and at least one of the blood and body fluid, a fluid feeding pump connected with the fluid feeding tube, a fluid discharge pump connected with the fluid discharge tube, a fluid feed rate adjusting means connected with one of the fluid feeding tube and fluid feeding pump and capable of adjusting the rate of intracorporeal feeding of the cancer therapeutic agent-containing extracoporeal medical fluid and at least one of the blood and body fluid, and a fluid discharge rate adjusting means connected with one of the fluid discharge tube and fluid discharge pump and capable of adjusting the rate of extracorporeal discharging of the cancer therapeutic agent-containing intracorporeal medical fluid and at least one of the blood and body fluid in a manner such that the amount of the fluid extracorporeally discharged may become larger than the amount of the fluid fed.

By doing so, it is possible to make the pressure on the fluid discharge side lower than that on the fluid feeding side in the system connecting the feeding side with the discharge side to thereby prevent the cancer therapeutic agent from leaking into the blood circulation system outside the pelvis while maintaining the effects of the anticancer agent on the cancer tissue or tissues.

The fluid discharge rate adjusting means is constituted so that the cancer therapeutic agent-containing medical fluid and at least one of the blood and body fluid can be discharged at a rate higher by at least 10 ml/min than the rate of feeding thereof.

By doing so, high cancer chemotherapeutic effects can be obtained while suppressing the adverse effects of the cancer therapeutic agent to the minimum.

At least one of an anticancer agent, a radioisotope, a gene used for gene therapy, a DNA molecule used for gene therapy, RNA molecule used for gene therapy or a cell used for gene therapy can be used as the cancer therapeutic agent.

By this, cancer can intensively be treated.

PREFERRED EMBODIMENTS OF THE INVENTION

Figure 1:
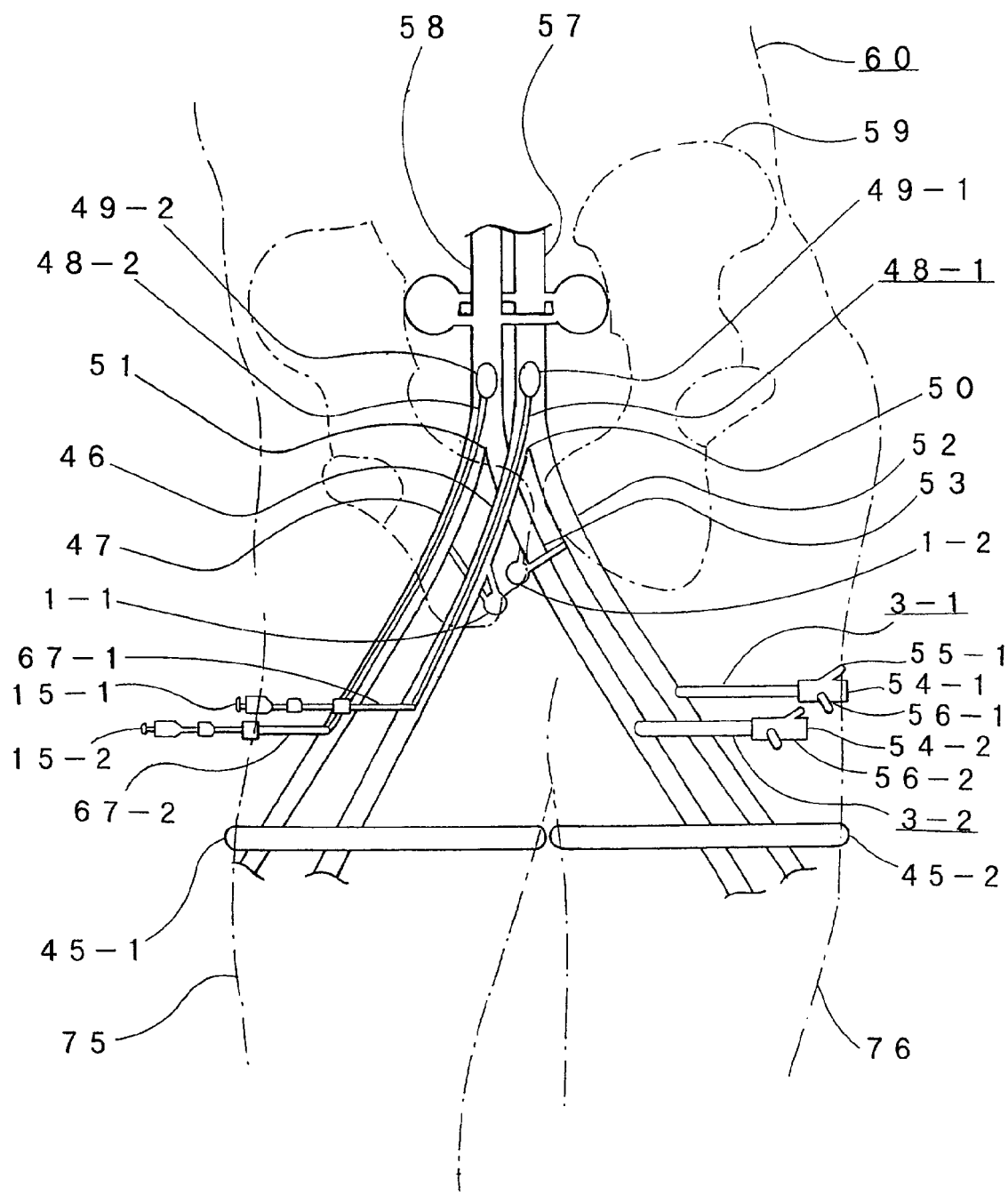
FIG. 1 is an explanatory drawing illustrating the cancer therapeutic agent perfusion therapy of the present invention.

In the following, preferred embodiments of the present invention are described referring to the drawings. The parts, materials thereof and disposition thereof and other constituent elements described hereinbelow are by no means limitative of the scope of the invention. It is a matter of course that various alterations and modification can be made thereto without departing the spirit of the present invention.

In particular, the sizes (French scale [Fr]) of catheters and other tubes as employed and described herein are given to suggest most suited ones in the embodiments of the invention and are not intended to restrict the scope of the invention.

In FIG. 1, there is shown an embodiment of the cancer therapeutic agent perfusion therapy according to the invention as applied to cancer tissues 1, which is an advanced cancer tissue located within the pelvis 59.

A patient 60 has advanced cancer tissues 1 at sites located within the pelvis 59.

The aorta 57 is branched into the right femoral artery 46 and left femoral artery 52 toward the inferior limbs, while the cava 58 is branched into the right femoral vein 47 and the left femoral vein 53 toward the inferior limbs.

The cancer tissue 1-1 is located between the right femoral artery 46 and the right femoral vein 47, while the cancer tissue 1-2 is located between the left femoral artery 52 and the left femoral vein 53.

A balloon catheter 48-1 as a first balloon catheter is percutaneously inserted into the aorta 57 through the right femoral artery 46 by means of an introducer 2, and a balloon catheter 48-2 as a second balloon catheter is percutaneously into the cava 58 through the right femoral vein 47 by means of an introducer 2.

A sheath 3-1 as a first sheath is percutaneously inserted into the left femoral artery 52 and a sheath 3-2 as a second sheath is percutaneously inserted into the left femoral vein 53.

Blood containing an anticancer agent as an example of the cancer therapeutic agent (not shown) is administered from a port A 54-1 mounted on the rear end of the sheath 3-1 whereas the blood containing the anticancer agent, among others, is recovered from a port A 54-2 mounted on the rear end of the sheath 3-2.

A tourniquet 45-1 is mounted around the right femoral region 75 at an adequate predetermined level to block the blood flow in the aorta 57 in that region of the inferior limb side artery which is below that predetermined level, and a tourniquet 45-2 is mounted around the left femoral region 76 at an adequate predetermined level to block the blood flow in the cava 58 in that region of the inferior limb side vein which is below that predetermined level.

A syringe 15-1 for inflating the balloon 49-1 is connected with the rear end of the balloon catheter 48-1, and a syringe 15-2 for inflating the balloon 49-2 is connected with the rear end of the balloon catheter 48-2. Physiological saline or the like (not shown) is included in the syringe 15-1 and syringe 15-2, respectively.

The advanced cancer tissues 1 are bladder cancer, uterus carcinoma tissues or rectal cancer, for instance. Bladder cancer is caused by canceration of the transitional epithelium covering the surface and rich in stretchability. While bladder cancer tends to occur inside the bladder, similar lesions may also be found in the urethra and renal pelvis, which are upstream in the direction of flow of urine, in some instances. Uterus carcinoma includes uterus sarcoma, cervical carcinoma and endometrial carcinoma, among others.

In the present embodiment, an anticancer agent is used as an example of a cancer therapeutic agent. However, a radioisotope, a gene for gene therapy, a DNA molecule for gene therapy, a RNA molecule for gene therapy and a cell for gene therapy may be used as a cancer therapeutic agent.

The anticancer agent is an agent destroying tumor cells and includes, among others, metabolic antagonists, alkylating agents, anticancer antibiotics, plant alkaloids and like classes of substances. The metabolic antagonists suppress the division of cancer cells by utilizing enzymes contained in large amounts in rapidly proliferating cancer cells. The alkylating agents are agents initially developed as poison gases and act on DNAs playing important roles in the substance of life, for example in genetic information transmission. An alkylating agent binds to a site of DNA where it damages the DNA and thereby kill a cancer cell. The anticancer antibiotics, like ordinary antibiotics, are derived from microorganisms in the soil. The plant alkaloids inhibit the function of microtubules, which are important in cell division, and thereby kill cancer cells. Among the anticancer agents acting on microtubules, there are such substances as paclitaxel. In the practice of the present invention, those agents which are generally called anticancer agents can be used without limitation.

As a radioisotope, $^{123}I$, $^{125}I$, $^{131}I$, $^{32}P$, $^{64}CU$, $^{211}At$, $^{177}Lu$, $^{90}Y$, $^{186}Re$, $^{212}Pb$, $^{212}Bi$ or the similar radioisotope itself, or a radiolabeled tumor-specific antigen can be used.

The radioisotope deprives a cell of its dividing and multiplying ability by directly acting on DNAs of the cell. Further, it kills tumor cells by inducing apoptosis. The radioisotope is used with mixed in physiologic saline or the like.

As a gene, a DNA molecule, a RNA molecule or a cell for gene therapy, those for cancer gene therapy can be used. The gene, the DNA molecule, the RNA molecule or the cell for gene therapy is used by itself or in combination with other agents. They inhibit the action of an oncogene, activate the devitalized action of the tumor suppressor gene, and potentiate immunity to the tumor. The gene, the DNA molecule, the RNA molecule and the cell are used with mixed in physiologic saline or the like.

As a gene for gene therapy, a tumor suppressor gene, a drug-metabolic-enzyme-gene or a DNA vaccine can be used.

As a tumor suppressor gene, p53 gene can be used. p53 gene inhibits the proliferation of cancer by being induced to the tumor cell whose tumor suppressor gene has been deleted or mutated.

A drug-metabolic-enzyme-gene is the gene used for suicide gene therapy. It originates in microorganism and does not normally exist in the cell of a mammal.

A prodrug, toxically activated by an enzyme produced when the drug-metabolic-enzyme-gene is induced to tumor cell, is administrated whereby only gene-transferred cells can be selectively killed. Generally, the prodrug is an antimicrobial agent such as an antiviral agent, an antifugal agent and the like.

In the present embodiment, a prodrug is fed into the body through cancer therapeutic agent-containing fluid feeder 42 after a drug-metabolic-enzyme-gene is fed into the body through cancer therapeutic agent-containing fluid feeder 42.

As a combination of the drug-metabolic-enzyme-gene and the prodrug, one of the following combinations can be used, herpes simplex virus thymidine-kinase (HSV-TK) and ganciclovir (GCV) or acyclovir (ACV), cytosine deaminase and 5-fluorocytosine (5-FC), varicella-zoster virus thymidine-kinase and 6-emetoxypurinearabinoside (ara-M), E. coli gpt and 6-thioxanthine (6-TX), and E. coli deoD and 6-methylpurine-2'-deoxyriboside (Mep-dR).

As a DNA molecule for gene therapy, antisenseoligodeoxinucleotide (antisense ODNs) can be used. Antisenseoligodeoxinucleotide is to inhibit the target oncogene expression and is a small DNA molecule which has a complementary base sequence with mRNA of the target tumor. The antisense inhibits protein biosynthesis by being hybridized with target mRNA in the cell to thereby inhibit the target gene expression.

As a RNA molecule for gene therapy, antisense RNA or ribozyme can be used.

Antisense RNA is to inhibit the target oncogene expression and to be made to express by antisense DNA (cDNA).

Ribozyme is a RNA molecule which has a breaking activity on the complementary mRNA. It is constituted of the antisense site and an active site carrying the breaking activity on the target mRNA. The active site breaks the target mRNA and protein biosynthesis is inhibited, whereby the target gene expression can be inhibited. Hummer-head type, hair-pin type or hepatitis D type ribozyme may be used in this embodiment.

A cell for gene therapy, an effector-cell induced a cytokine gene can be used.

As a cytokine gene, a tumor necrosis factor (TNF), interferon-γ (INF-γ), FCR, TCR, IL-2R, IL-2, IL-7 or IL-12 can be used.

As an effector-cell, tumor-infiltrating lymphocytes(TIL), LAK cell or cytotoxic T lymphocytes(CTL) can be used.

The gene, the DNA molecule, the RNA molecule and the cell for gene therapy do not limited to those mentioned above, other gene, DNA molecule, RNA molecule and cell may be used.

The body fluid to be recovered from the body includes all body fluid species contained in the body, such as blood and lymph. Hereinafter, the body fluid recovered or to be recovered from the body is referred to as "blood or the like".

Figure 2:
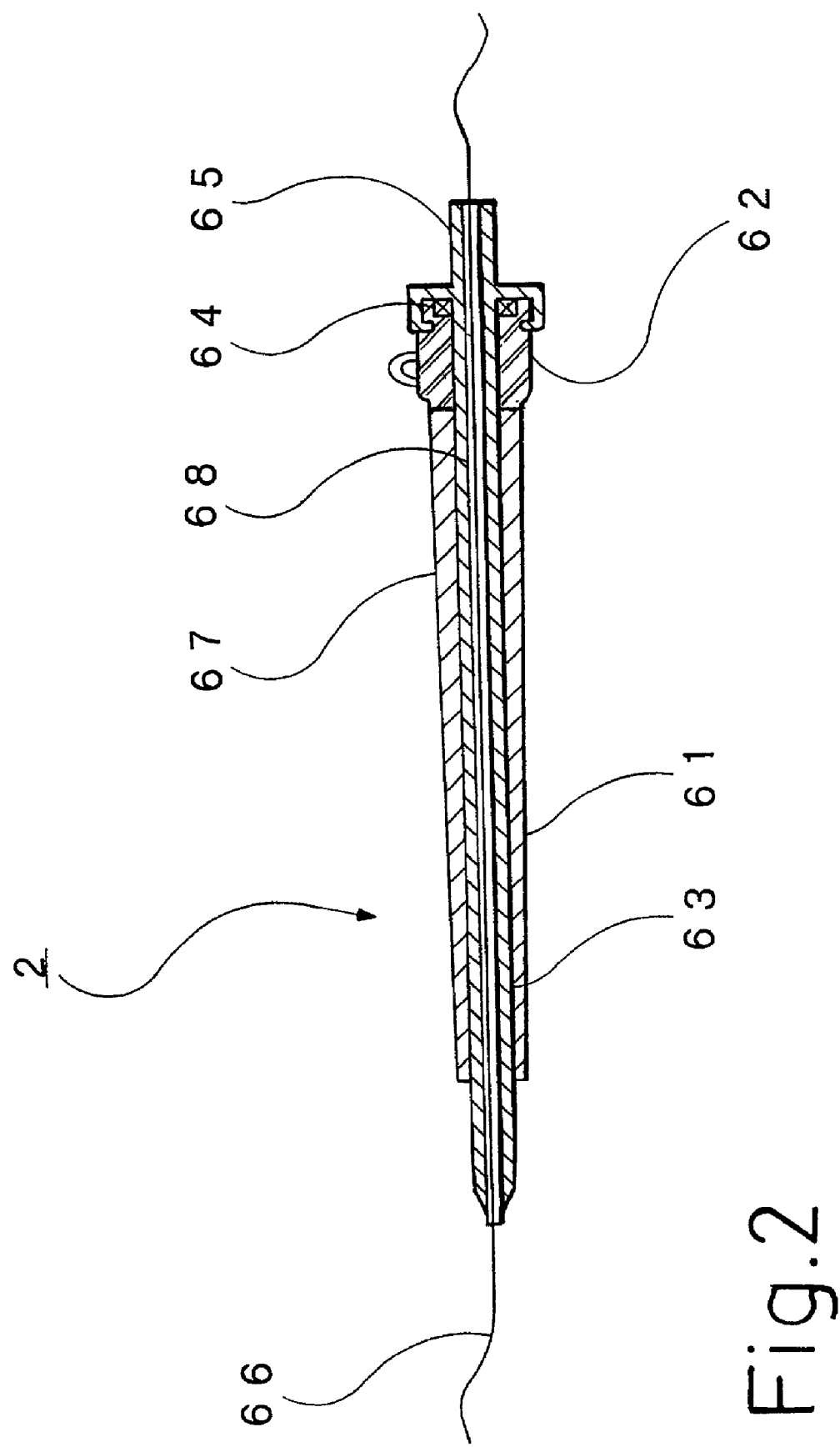
FIG. 2 is a sectional view of an introducer.

The constitution of an introducer 2 is shown in FIG. 2. The introducer 2 comprises a sheath 67 for the passage of a catheter, a dilator 65 and a guide wire 66 and is used as a guide into the blood vessel when the balloon catheter 48-1 is percutaneously inserted into the aorta 57 through the right femoral artery 46 or when the balloon catheter 48-2 is percutaneously inserted into the cava 58 through the right femoral vein 47.

The catheter passage sheath 67 comprises a flexible or rigid tubular body 61 made of PTFE (polytetrafluoroethylene) or the like and a connector 62 attached to the rear end of the tubular body 61. The tubular body 61 has a passage 63, through which the tip of the tubular body 61 communicates with the rear end of the connector 62. The rear end of the connector 62 is provided with a hemostatic valve 64 to prevent blood from overflowing from the blood vessel through which the catheter passage sheath 67 has been inserted and in which it is indwelled.

The dilator 65 is a device for preventing the tubular body 61 from kinking on the occasion of insertion of the introducer 2 into the blood vessel. The tip of the dilator 65 communicates with the rear end side thereof and has a tubular passage 68 for the passage of the guide wire 66 therethrough. The rear end of the dilator 65 is fitted with the connector 62.

The introducer 2 is constituted as mentioned above. In the following, a procedure is described for securing a passage for percutaneous insertion of the balloon catheter 48-1 into the aorta 57 through the right femoral artery 46 using the introducer 2.

Before using the introducer 2, the skin corresponding to the site of the right femoral artery 46 is slightly incised by a method known in the art and the guide wire 66 is inserted into the right femoral artery 46 through the incision and allowed to indwell at an adequate predetermined position.

The tip of the introducer 2 is percutaneously inserted, from the rear end side of the guide wire 66, into the right femoral artery 46 so that the guide wire 66 may pass through the tubular passage 68 of the dilator 65, and allowed to indwell therein.

The guide wire 66 is taken out of the body through the right femoral artery 46 and then the dilator 65 is disengaged from the connector 62, and the dilator 65 is extracorporeally drawn out of the passage 63 of the catheter passage sheath 67. In this way, the tip of the catheter passage sheath 67 is percutaneously indwelled in the right femoral artery 46.

In such a manner as mentioned above, a passage for inserting the balloon catheter 48-1 into the aorta 57 through the right femoral artery 46 is secured in the right femoral artery 46 using the introducer 2.

The procedure for securing a passage for percutaneously inserting the balloon catheter 48-2 into the cava 58 through the right femoral vein 47 is the same as mentioned above. Thus, the tip of the introducer 2 is percutaneously inserted into the right femoral vein 47 and the tip of the catheter passage sheath 67 is percutaneously indwelled in the right femoral vein 47.

Figure 3:
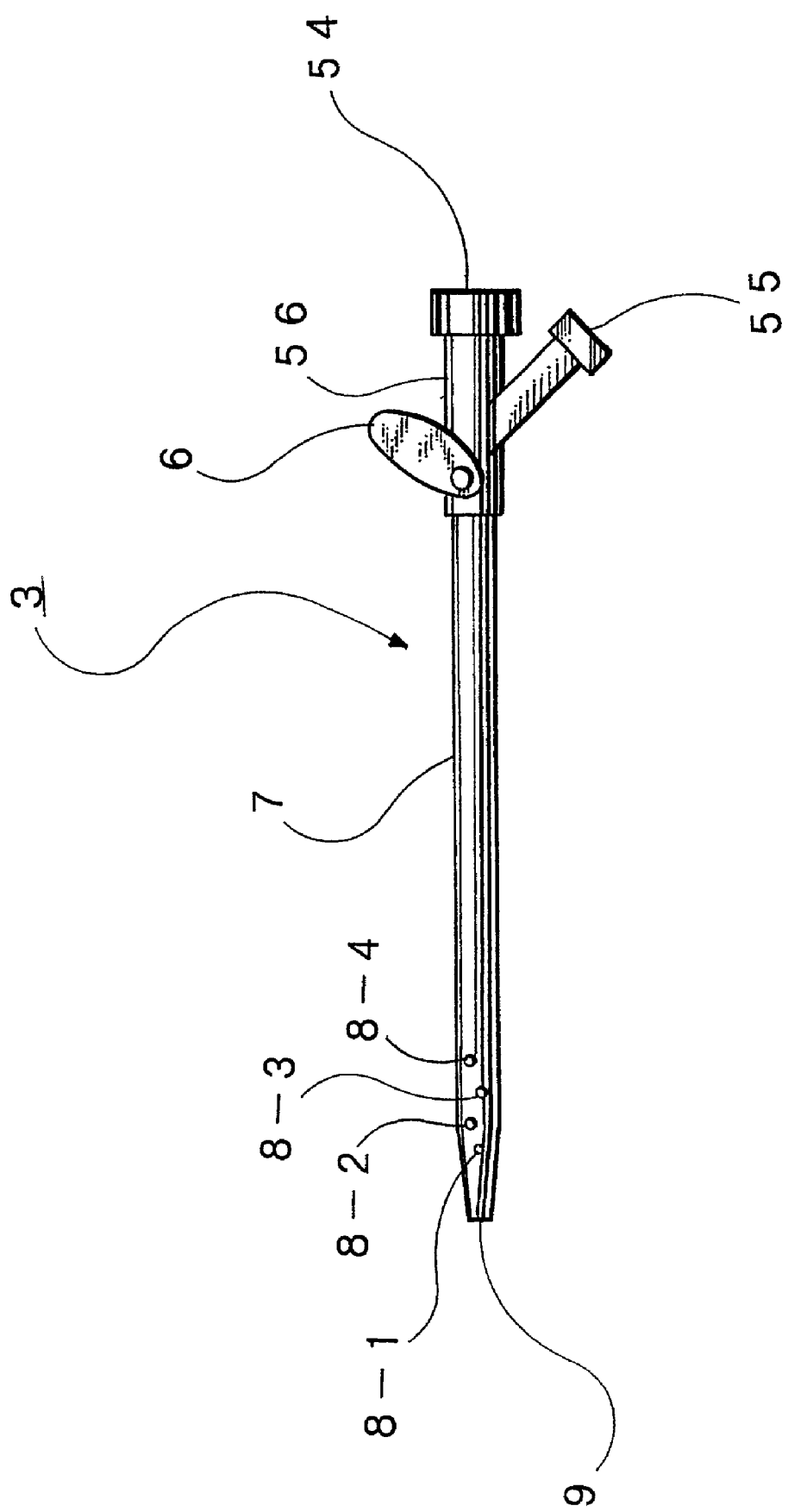
FIG. 3 is a sectional view of a sheath.

The constitution of a sheath 3 is shown in FIG. 3. The sheath 3 comprises a three-way cock 56 and a flexible or rigid tubular body 7 made of PTFE or the like. The sheath 3-1 (FIG. 1) is used as a tool for administering a predetermined dose of a cancer therapeutic agent into the closed region within the aorta 57, and the sheath 3-2 (FIG. 1) is used as a tool for recovering a larger amount, as compared with the dose of the cancer therapeutic agent, of the cancer therapeutic agent-containing body fluid from the closed region within the cava 58.

The three-way cock 56 is provided with a port A 54 and a port B 55 and the port A 54 or port B 55, upon change-over operation of a selector lever 6, is allowed to alternately communicate with side openings 8 made at the tip of the tubular body 7 and with a pointed end hole 9.

The port A 54 is connected with a fluid feeding tube or a fluid discharging tube of an extracorporeal blood circulation apparatus, which is to be described later herein, for intracorporeally feeding a medical fluid, blood or the like or discharge the same from the body. The port B 55 is connected with a syringe or the like (not shown) for intracorporeally feeding a necessary agent or agents, for example a contrast medium, an anticoagulant and/or a hemolytic agent.

The balloon catheter 48-1, together with the tourniquet 45-1 to be described later herein, serves to form a closed arterial region for the formation of an intraarterial closed region between an adequate position in the aorta 57 and an artery site on the lower limb side. The balloon catheter 48-2 forms, together with the tourniquet 45-2, a closed venous region for the formation of an intravenous closed region between an adequate position in the cava 58 and a vein site on the lower limb side.

The balloon catheter 48 to be used is a balloon catheter 10 of the type claimed in claim 1 or a balloon catheter 16 of the type claimed in claim 3.

Figure 4:
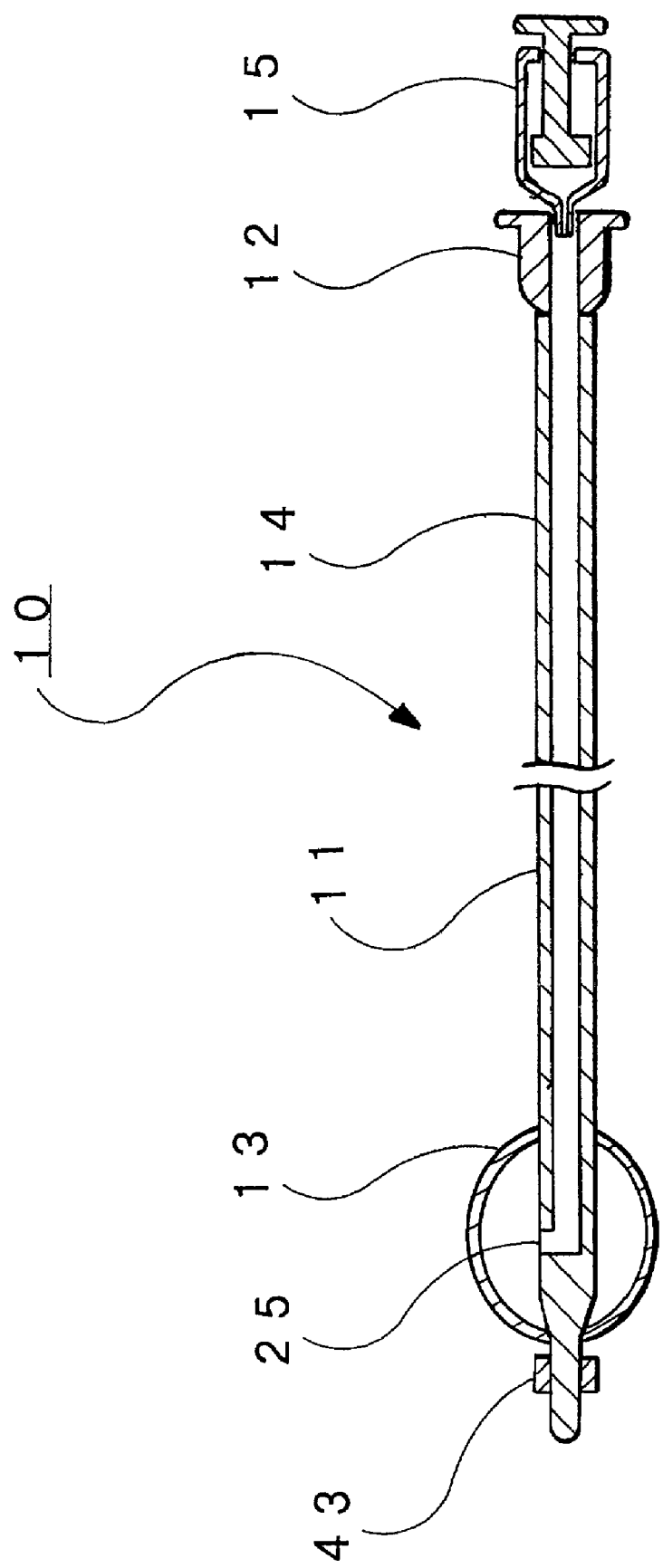
FIG. 4 is a sectional view of a balloon catheter.
Figure 5:
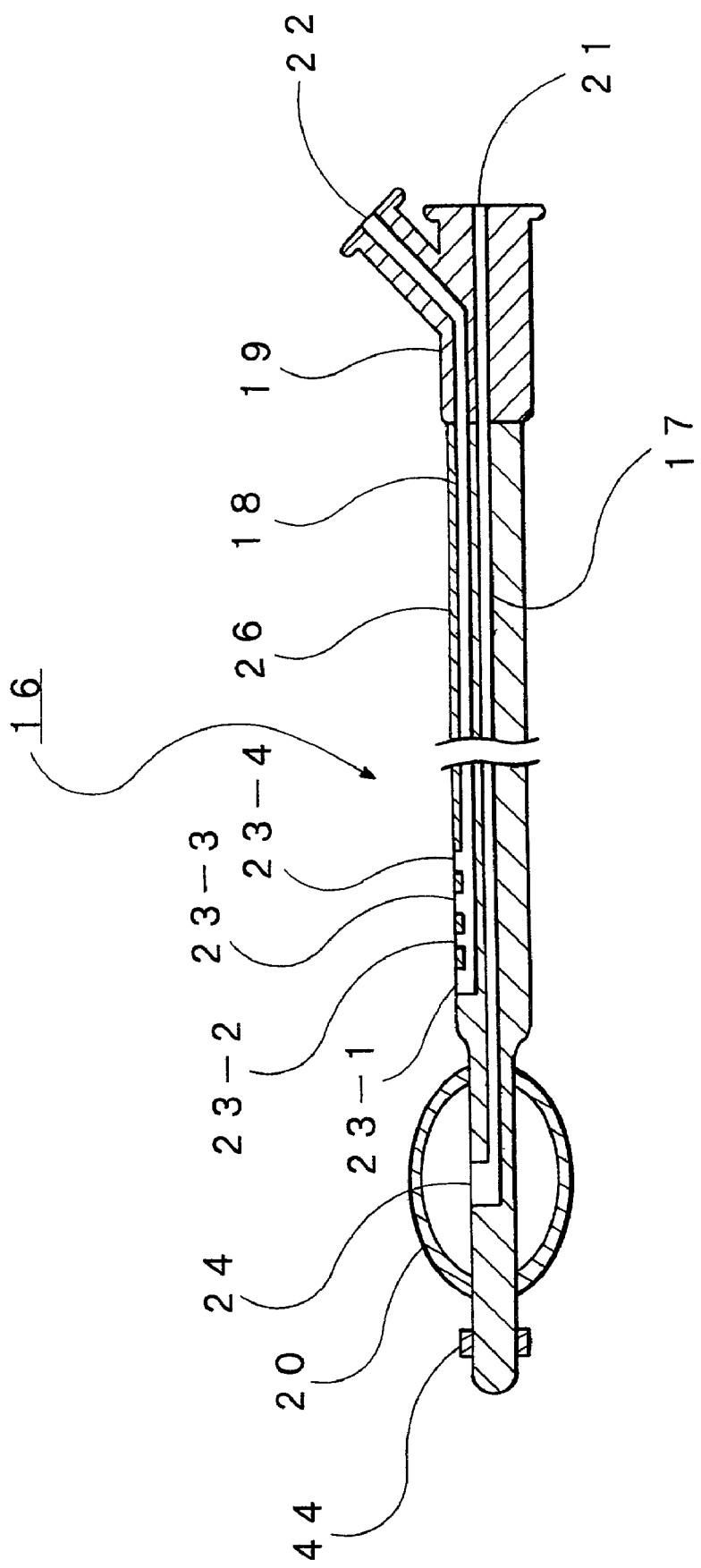
FIG. 5 is a sectional view of another balloon catheter.

The constitution of the balloon catheter 10 is shown in FIG. 4 and the constitution of the balloon catheter 16 is shown in FIG. 5. The balloon catheter 10 and balloon catheter 16 are described below one by one.

The balloon catheter 10 comprises a basal part 11, which is a flexible body, a connector 12 with which a syringe 15 is connected, an inflatable balloon 13, a tubular passage 14 provided within the basal part 11 and connecting the rear end of the connector 12 with a balloon-inflating opening 25 located in the middle of the balloon, and a front coil marker 43.

The balloon 13 is made of freely blown polyethylene, polyethylene terephthalate, nylon, polyester or a like resin. A syringe 15 containing physiological saline or the like (not shown) is connected with the connector 12 on the ready-to-hand side thereof When an operator applies a pressure to the syringe 15, the balloon 13 is inflated and the circumference of the balloon 13 comes into close contact with the blood vessel inside wall, whereby the blood flow is blocked at the blood vessel site.

The front coil marker 43 is made of a radiopaque material, such as titanium, so that the operator can grasp the position of the tip of the balloon catheter 10 on the occasion of intervention under radioscopy.

By providing the front coil marker 43, it becomes possible to selectively advance the balloon 13 until the intended site in carrying out angiography under X-ray fluoroscopy while confirming the position of the front coil marker 43.

While the balloon catheter 10 in the above-mentioned embodiment of the invention, which is to be applied to the femoral artery and vein, is constituted so that it can be inserted into the blood vessel as itself without using any guide wire, it may have an overwire type, RX type or monorail type constitution.

Now, the balloon catheter 16 is described referring to FIG. 5. The balloon catheter 16, which is to be used in another embodiment of the cancer therapeutic agent perfusion therapy according to the present invention, has the functions of the sheath 3 in addition to the functions of the balloon catheter 10. The constitution thereof is explained below.

The balloon catheter 16 comprises a basal part 26, which is a flexible body, a connector 19, an inflatable balloon 20, a front coil marker 44, a tubular passage A 17 provided within the basal body 26 and connecting a port A 21 provided at the rear end of the connector 19 with an balloon-inflating opening 24 located in the middle of the balloon 20, and a tubular passage B 18 connecting a port B 22 provided at the rear end of the connector 19 with side openings 23 made at the tip of the basal part 26.

By indwelling the balloon catheter 16 within the blood vessel at an adequate predetermined site and inflating the balloon 20 to thereby bringing the circumference of the balloon 20 into close contact with the blood vessel inside wall, it is possible to form a hemostatic region in that blood vessel. On that occasion, a syringe or the like containing a necessary medical fluid (not shown) is connected with the port B 22, whereby the necessary medical fluid can be fed to the hemostatic region from the side openings 23 via the tubular passage B 18. By connecting an aspirating device, such as a syringe, with the port B 22, it is also possible to drain blood or the like from the hemostatic region.

Like the balloon catheter 10, the balloon catheter 16 may also have an overwire type, RX type or monorail type constitution. A front coil marker 44 is also provided at the tip of the basal part 26 and, thus, intravascular controlling can selectively be performed under X ray fluoroscopy.

As mentioned above, the balloon catheter 16 makes it possible to effect blood flow blocking by inflating the balloon and carry out intracorporeal administration of an agent and recover of the same from the body by the single use thereof, so that the number of tools to be percutaneously inserted into the body or blood vessel of a patient 60 and indwelled therein can be reduced.

The tourniquet 45-1 is mounted on the right femur 75 to block the blood flow at a lower limb artery site below the predetermined site within the aorta 57, and the tourniquet 45-2 is mounted on the left femur 76 to block the blood flow at a lower limb vein site lower than the predetermined site within the cava 58.

When the above balloon catheter 10 or balloon catheter 16 is used in combination therewith, the tourniquet 45-1 forms an intraarterial closed region between the predetermined position within the aorta 57 and the lower limb side artery site and the tourniquet 45-2 forms an intravenous closed region between the predetermined position within the cava 58 and the lower limb side vein site.

Since the tourniquet 45 is well known in the art, any detailed mention referring to a drawing is not made herein. Generally, it comprises an inner tube inflatable when pressurized by an pressuring means (not shown), a cuff for fixing the inner tube after winding the same around a lower limb at an adequate level, and a cuff hose for sending air or a like fluid from the pressuring means into the inner tube.

For blocking the blood flow using the tourniquet 45, air or a like fluid is sent from the pressurizing means into the inner tube through the cuff hose, whereby the inner tube is pressurized and inflated and presses against the circumference of the lower limb at surrounded by the tube and, as a result, the blood flow toward the periphery is blocked.

Figure 6:
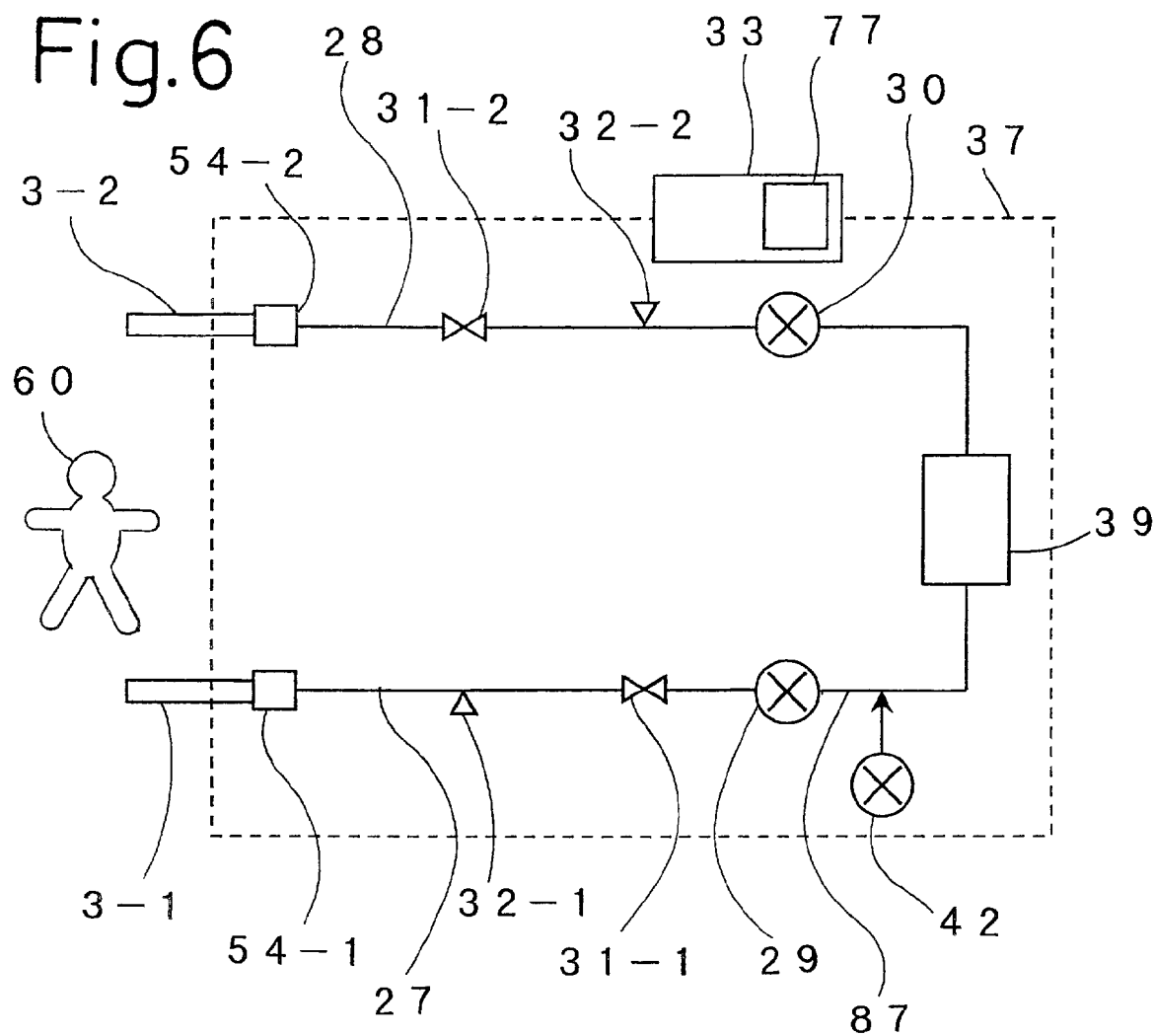
FIG. 6 is a block diagram illustrating a cancer therapeutic agent perfusion apparatus A according to the invention.

The constitution of the cancer therapeutic agent perfusion apparatus A 37, as an extracorporeal blood circulation system, according to the present invention is shown in FIG. 6.

As shown in FIG. 6, the cancer therapeutic agent perfusion apparatus A 37 comprises a fluid-feeding tube 27, a fluid discharging tube 28, a fluid feeding pump 29, a fluid discharging pump 30, constant flow valves 31, flow rate sensors 32, a controller 33, a reservoir 39, a cancer therapeutic agent feeder 42, a blood circuit 87 and a settings display panel 77.

The feeding tube 27 as a fluid feeding tube and the fluid discharge tube 28 as a drainage tube each is a transparent and flexible tube made of a synthetic resin such as a silicone rubber.

The tip side of the fluid feeding tube 27 is connected with the port A 54-1 of the sheath 3-1. The tip side of the fluid discharging tube 28 is connected with the port A 54-2 of the sheath 3-2.

Figure 9:
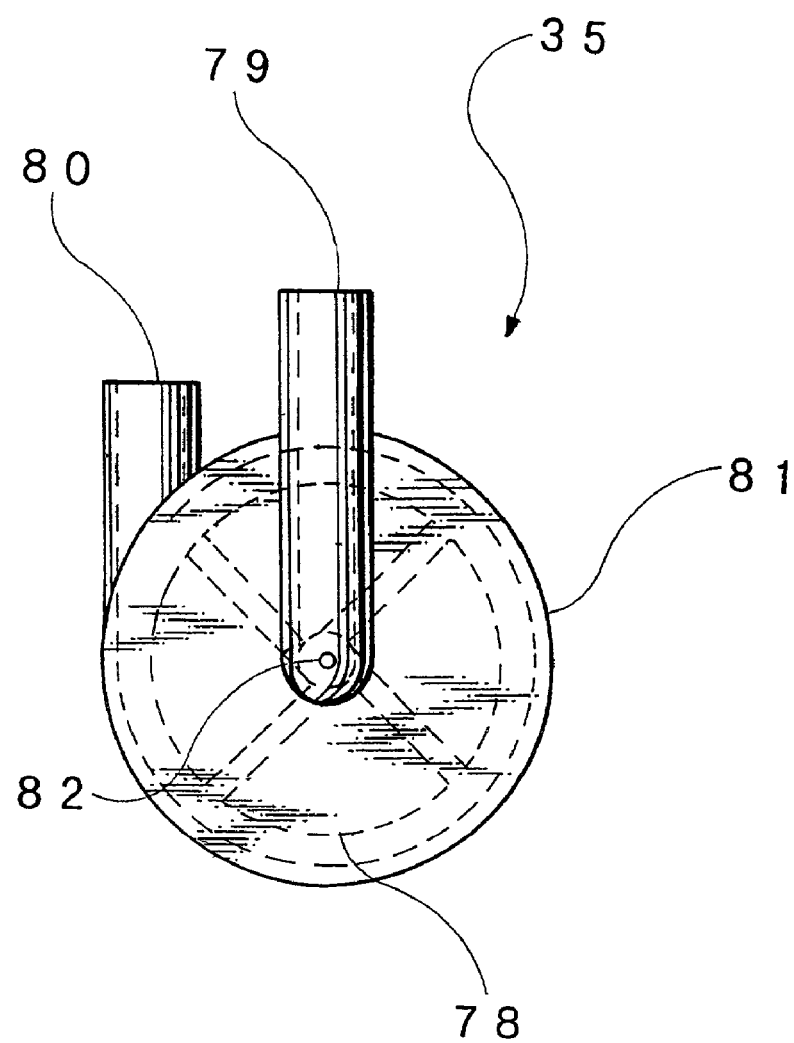
FIG. 9 is a drawing illustrating the constitution of a centrifugal pump.

The feeding pump 29 as a fluid feeding pump and the discharge pump 30 as a fluid drainage pump can feed or discharge a fluid under a constant pressure and each comprises a centrifugal pump 35 as shown in FIG. 9.

As shown in FIG. 9, the centrifugal pump 35 sucks a fluid from the inlet port 79 and discharges the fluid from the discharge port 80 when a centrifugal fan 78 contained in a casing 81 is rotated with the shaft 82 of a motor (not shown) as an axis.

The feeding pump 29 and discharge pump 30 each may be of any type capable of feeding or discharging a fluid at a constant pressure and may be constituted, for example, of a turbine pump, screw pump or the like. It may be constituted of a roller pump giving pulsations.

As shown in FIG. 6, the feeding pump 29 and discharge pump 30 are driven under the control of the controller 33, and blood or the like can be discharged through the discharge tube 28 under the sucking action of the discharge pump 30 and blood or the like can be fed into the body through the feeding tube 27 under the discharging action of the feeding pump 29.

The controller 33 drives and controls the feeding pump 29, discharge pump 30, constant flow valve 31 and cancer therapeutic agent feeder 42 according to the values preset by the operator. Externally, it also has a settings display panel 77 and, internally, it has a CPU, ROM, etc. Furthermore, it is provided with an operating state indicating lamp, caution lamp, emergency stop switch, tube disconnection warning lamp, bubble detection lamp and so forth (not shown).

Figure 10:
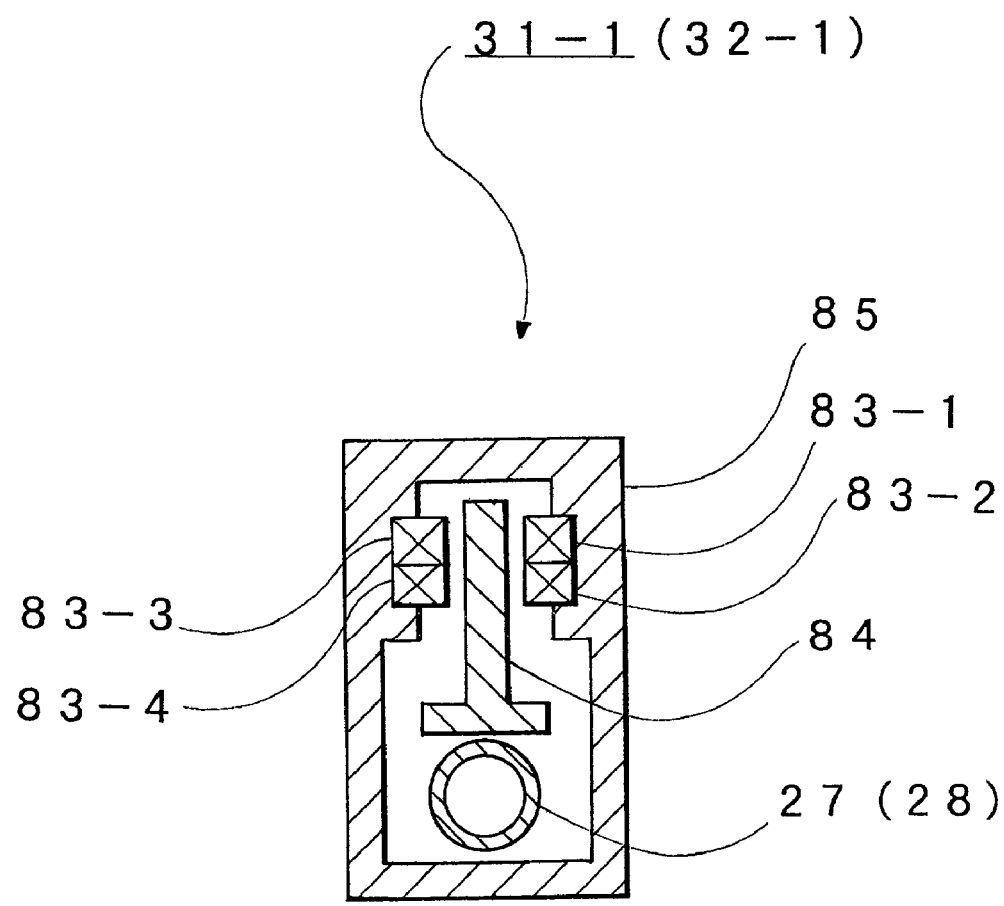
FIG. 10 is a sectional view of a constant flow valve.

The constitution of the constant flow valve 31-1 as means for adjusting the rate of fluid feeding is shown in FIG. 10. FIG. 10 is a sectional view as seen in the direction of the flow channel of the constant flow rate valve 31-1. The constant rate valve 31-1 is clamped surrounding the feeding tube 27.

As shown in FIG. 10, the magnetic force of coils 83 changes according to the controlling current from the controller 33 and a plunger 84 is pressed against the feeding tube 27 by the magnetic force of the coils 83, whereby the sectional area of the feeding tube 27 is changed and thereby the fluid feeding rate is adjusted.

When no current flows through the coils 83, the plunger 84 is kept in a neutral position by means of a stator yoke 85 made of a soft magnetic material and the feeding tube 27 is in an opened state. The constant flow valve 31-1 may be constituted of a solenoid valve in which a rotary solenoid is used, namely a rotary valve structure is driven by means of an electromagnetic solenoid.

The constant flow valve 31-2 as the discharge adjusting means is clamped around the discharge tube 28 and adjusts the rate of discharge through the discharge tube 28.

The constant flow valve 31-2 also has the same constitution as the constant flow valve 31-1 shown in FIG. 10, hence no detailed mention thereof is made herein.

As shown in FIG. 6, the reservoir 39 reserves the blood or the like discharged. The blood or the like reserved in the reservoir 39 is drawn by means of the feeding pump 29 and discharged on the feeding tube 27 side.

The cancer therapeutic agent feeder 42 sends a cancer therapeutic agent-containing fluid into the blood circuit 87. It comprises a syringe pump and driven and controlled by the controller 33.

The syringe pump has a worm gear or a ball screw structure and can discharge a predetermined amount of the medical fluid contained in the syringe when the plunger of the syringe is constantly thrust into the barrel by means of a slider without moving the syringe body itself.

The cancer therapeutic agent fed into the blood circuit 87 is sent into the body by the suction and discharge action of the feeding pump 29.

It is also possible to fill fluid feeders similar to the cancer therapeutic agent feeder 42 with necessary medical fluids, such as an infusion fluid, physiological saline and an anticoagulant, respectively and place them as annexes to the blood circuit 87, whereby the blood circuit 87 can be caused to contain the infusion fluid, physiological saline, anticoagulant and other necessary agents each in a predetermined amount. By doing so, it becomes possible to arbitrarily preset and control the proportions of the necessary agents, cancer therapeutic agents, blood and the like to be fed into the body.

The flow rate sensors 32 each is constituted of a Doppler type ultrasonic current meter capable of measuring the fluid feeding rate and fluid discharging rate without directly contacting the cancer therapeutic agent, blood or the like. There are other methods of flow rate measurement using ultrasonic waves than the Doppler method, for example the time difference method and SING-AROUND method. These may also be employed in constituting the sensors.

The flow rate sensors 32 each has therewithin a sending side piezoelectric element (not shown) for generating ultrasonic waves and a receiving side piezoelectric element (not shown) for receiving the Doppler signal. It transmits ultrasonic waves from the sending side piezoelectric element to the blood or the like flowing in the feeding tube 27 or discharging tube 28 and receives, through the receiving side piezoelectric element, the Doppler signal obtained in response to the flow rate of the blood or the like.

The Doppler signal received is amplified in an amplifier (not shown) and, after removal of high-frequency components by a low-pass filter, is transmitted, as a measured value corresponding to the flow rate, to the controller 33.

In the embodiment shown, the flow rate sensor 32-1 and flow rate sensor 32-2 are disposed around the feeding tube 27 and discharging tube 28, respectively. It is also possible to dispose the flow rate sensor 32-1 in a flow channel (not shown) within the feeding pump 29 in place of the surroundings of the feeding tube 27 and dispose the flow rate sensor 32-2 in a channel (not shown) within the discharge pump 30 in place of the surroundings of the discharging tube 28.

Figure 11:
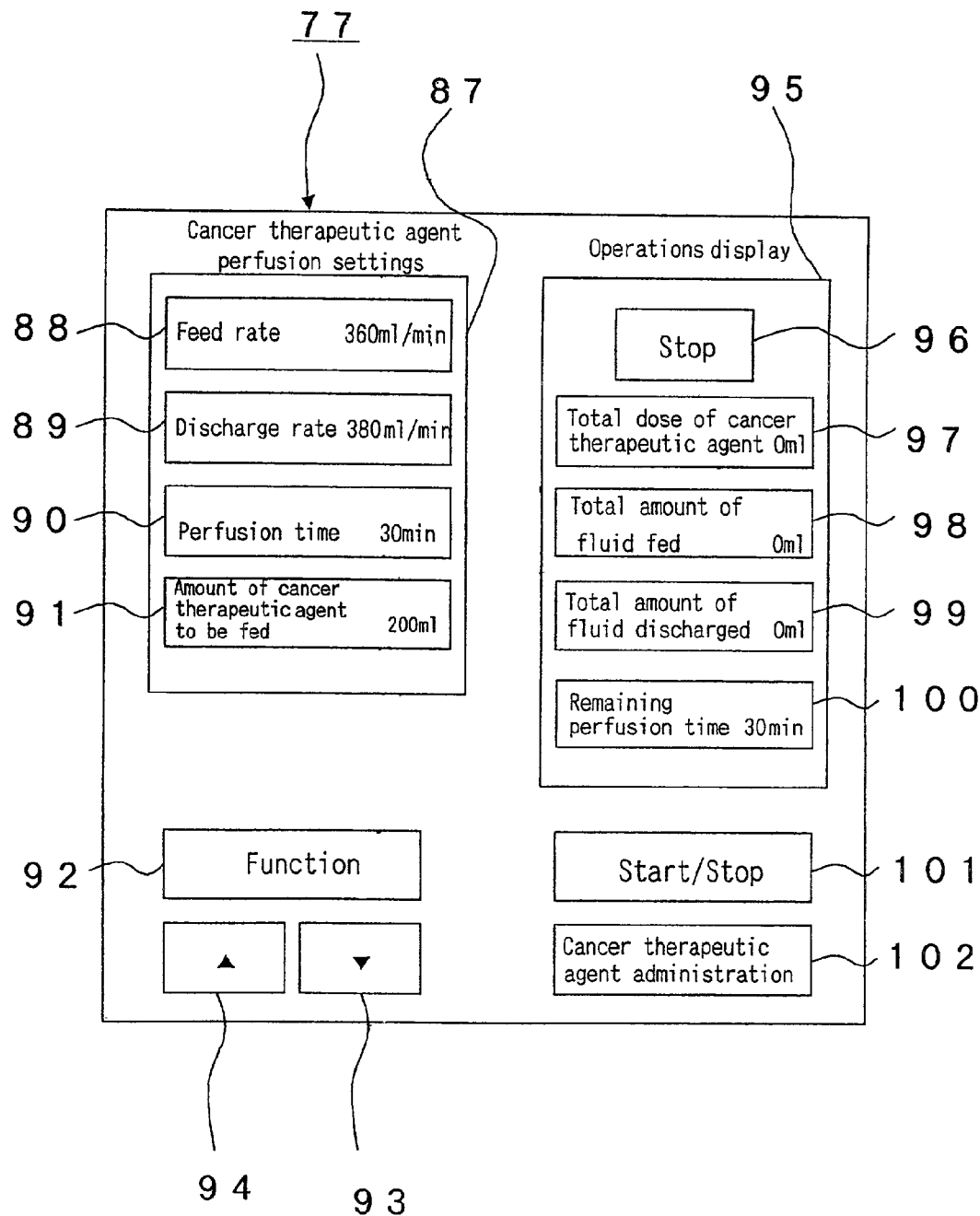
FIG. 11 is a top view of a setting display panel.

As shown in FIG. 11, the settings display panel 77 is a screen for presetting various values and so forth in carrying out the cancer therapeutic agent perfusion therapy and for confirming the operating conditions. It comprises a cancer therapeutic agent perfusion settings display 87, an operations display 95, an operation switch 101 and a cancer therapeutic agent administration key 102.

The cancer therapeutic agent perfusion settings display 87 comprises a feed rate setting display 88 for displaying the "preset fluid feeding rate" of the cancer therapeutic agent-containing blood or the like, a discharging rate setting display 89 for displaying the "preset discharge rate" of the blood or the like, a perfusion time setting display 90 for displaying the "preset perfusion time", and a cancer therapeutic agent feeding amount setting display 91 for displaying the "preset amount of the cancer therapeutic agent" to be fed into the body within an arbitrary time period during operation.

It is possible, by pushing a function key 92, to change the set value item which can be inputted in the order of feed rate setting display 88, discharge rate setting display 89, perfusion time setting display 90 and cancer therapeutic agent feed amount setting display 91.

The above preset values can be changed and reset by continuously varying the indicated value by means of an up key 93 and a down key 94.

Signals based on the preset values of the feed rate setting display 88, discharge rate setting display 89 and perfusion time setting display 90 are transmitted to the controller 33, and the controller 33 can drive and control the predetermined operations of the feeding pump 29, discharge pump 30, constant flow valve 31-1 and constant control valve 31-2 so that the predetermined amount of blood or the like may be perfused within the predetermined period of time.

By operating the cancer therapeutic agent administration key 102 at an arbitrary time during operation, it is possible for a signal based on the "cancer therapeutic agent feed amount setting" displayed on the cancer therapeutic agent feed amount display 91 to be transmitted to the controller 33, and the controller 33 can drive and control the cancer therapeutic agent feeder 42 to perform the predetermined working.

In starting the process, the operation switch 101 is pushed, whereupon a signal based on the "cancer therapeutic agent perfusion time setting" on the cancer therapeutic agent feed amount display 91 is transmitted to the controller 33 and the controller 33 drives and controls the cancer therapeutic agent feeder 42 to perform the predetermined working thereof.

The operations display 95 displays the states of the respective workings during process operation and includes a running/stop display 96 for displaying whether the process is running or is not running, a total cancer therapeutic agent dose display 97 for displaying the total amount of the cancer therapeutic agent fed, a total fluid feed amount display 98 for displaying the total amount of blood or the like fed, a total fluid discharge amount display 99 for displaying the total amount of blood or the like discharged, and a remaining perfusion time display 100 for displaying the remaining time of perfusion.

The indicated value on the total cancer therapeutic agent dose display 97 is determined by the "feed rate setting" on the cancer therapeutic agent feed amount setting display 91 and the number of operations of the cancer therapeutic agent administration key 102, and it indicates the total amount of the cancer therapeutic agent administered.

The indicated value on the total fluid feed amount display 98 is calculated from the value measured by the flow rate sensor 32-1, and the indicated value on the total fluid discharge amount display 99 is calculated from the value measured by the flow rate sensor 32-2.

The working of cancer therapeutic agent perfusion apparatus A 37 is now explained as an example of using an anticancer agent as a cancer therapeutic agent.

The operator performs the "fluid feed rate setting", "fluid discharge rate setting", "perfusion time setting" and "cancer therapeutic agent feed amount setting" using the settings display panel 77.

As examples of the working conditions, "360 ml/min" is taken as the "fluid feed rate setting" to be displayed in the feed rate setting display 87, "380 ml/min" as the "discharge rate setting" to be displayed on the discharge rate setting display 88, "30 min" as the "perfusion time setting" to be displayed on the perfusion time setting display 90, and "200 ml" as the "cancer therapeutic agent feed amount setting" to be displayed on the cancer therapeutic agent feed amount setting display 91. These setting can be modified during working of the apparatus according to the symptom of the patient and other conditions.

After setting cancer therapeutic agent perfusion conditions, the cancer therapeutic agent perfusion apparatus A 37 is started by pushing the operation switch 101. Thus, based on the cancer therapeutic agent perfusion settings using the cancer therapeutic agent perfusion settings display 87, the controller 33 drives and controls to start the feeding pump 29, the discharge pump 30, the constant flow valve 31 and the cancer therapeutic agent feeder 42. The running/stop display 96 changes from "stop" to "running".

As shown in FIG. 6, 200 ml of an anticancer agent-containing fluid is fed to the blood circuit 87 from the cancer therapeutic agent feeder 42 and the anticancer agent is fed to the feeding tube side 27 by the suction and discharge actions of the feeding pump 29.

The anticancer agent sent into the feeding tube 27 is adjusted to a flow rate of 360 ml/min by the discharge action of the feeding pump 29 and the flow rate control by the constant flow valve 31-1 and sent into the body via the sheath 3-1.

The flow rate sensor 32-1 measures the flow rate of the anticancer agent sent to the feeding tube 27 and transmits a signal corresponding to the flow rate to the controller 33. If the flow rate-reflecting signal shows a deviation greater than a predetermined range from the preset value of the "fluid feeding rate setting", the controller 33 controls the feeding pump 29 and the constant flow valve 31-1 in a feedback manner, whereby the preset rate of the "fluid feeding rate setting" is recovered and maintained.

The feeding pump 29 is driven and the anticancer agent fed from the feeding tube 27 is perfused intracoporeally, while the discharge pump 30 is driven and the anticancer agent-containing blood or the like is discharged through the discharging tube 28.

The flow rate sensor 32-2 measures the flow rate of the blood or the like discharged through the discharging tube 28 and transmits a signal corresponding to the flow rate to the controller 33.

Based on the flow rate-reflecting signal, the controller 33 controls the discharge pump 30 and the constant flow valve 31-2 in a feedback manner so that the preset rate of the "fluid discharging rate setting" is maintained.

The blood or the like discharged and sent through the discharging tube 28 is reserved in the reservoir 39 by the suction and discharge actions of the discharge pump 30.

The blood or the like stored in the reservoir 39 is sent to the feeding tube 27 side by the suction and discharge actions of the feeding pump 29, and the blood or the like sent to the feeding tube 27 is adjusted to the flow rate of 360 ml/min by means of the constant flow valve 31-1 and sent into the body via the sheath 3-1.

When the cancer therapeutic agent administration key 102 is operated at an arbitrary but adequate time point during operation, the cancer therapeutic agent feeder 42 sends 200 ml of the anticancer agent-containing fluid to the blood circuit 87 based on the reset value of the cancer therapeutic agent feed amount setting display 91.

The anticancer agent fed to the blood circuit 87 is mixed with the blood or the like sent from the reservoir 39 by the suction and discharge actions of the feeding pump 29. The thus-obtained blood or the like admixed with the anticancer agent is again adjusted to the flow rate of 360 ml/min by the discharge action of the feeding pump 29 and the flow rate control by the constant flow valve 31-1 and sent into the body via the sheath 3-1.

Based on the content of the anticancer agent in blood as measured by a method well known in the art, such as testing of the blood stored in the reservoir 39 by centrifugation, or urinalysis, the operator can arbitrarily modify the anticancer agent feeding rate and/or determine the frequency of dosing during perfusion.

After a predetermined period of the above anticancer agent perfusion, the counter (not shown) in the controller 33 works and the controller 33 stops the workings of the feeding pump 29, discharge pump 30, constant flow valves 31 and the cancer therapeutic agent feeder 42, whereupon the running/stop display 96 changes from "running" to "stop".

Figure 7:
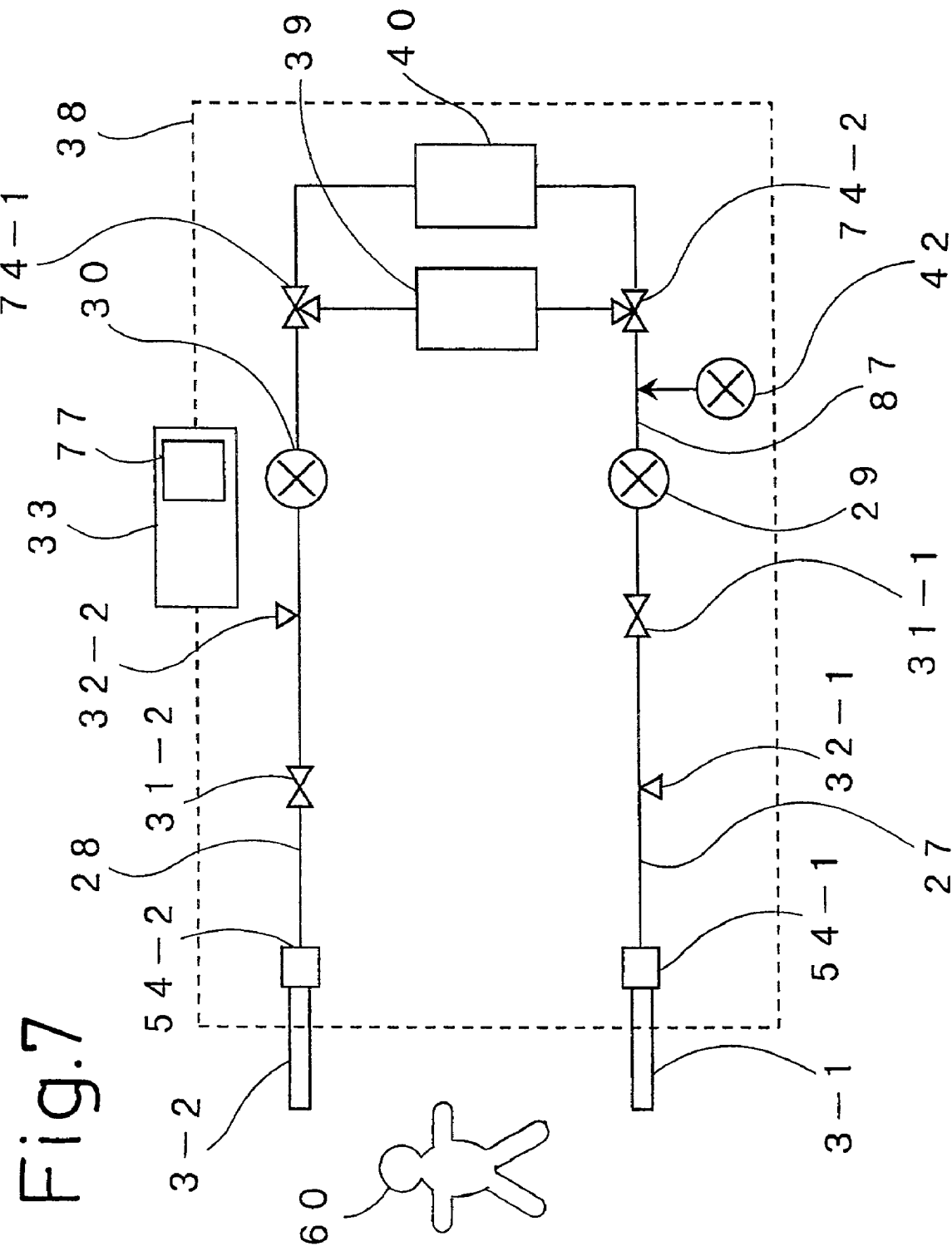
FIG. 7 is a block diagram illustrating another cancer therapeutic agent perfusion apparatus B according to the invention.

When a blood cleaning device 40 and three-way solenoid valves 74 are provided as in cancer therapeutic agent perfusion apparatus B 38 as shown in FIG. 7, it is possible to clean the blood discharged and send back the cleaned blood into the body for intracorporeal perfusion.

The cancer therapeutic agent perfusion apparatus B 38 has the same main constituent element as used in the cancer therapeutic agent perfusion apparatus A 37 and is constituted such that the blood cleaning device 40 and three-way solenoid valves 74 are further connected to the cancer therapeutic agent perfusion apparatus A 37.

The blood cleaning device 40 may constituted as a hemodialyzer in which a dialyzer having a dialysis membrane, such as a cellulose membrane, is used and the blood is diffused and filtered under an osmotic pressure between the blood and an electrolyte solution. In the hemodialyzer, the anticancer agent is removed and necessary components such as Ca and $HCO_3$ are supplemented.

The blood cleaning device 40 may be constituted also as a hemofiltration device in which the blood or the like is filtered and supplemented with substitute fluids, or as a hemoabsorption device in which the anticancer agent is removed by absorption on an absorptive substance having high affinity for the anticancer agent if the characteristics of the anticancer agent are suited therefore, or as a centrifuge for separating the blood into components and thereby separating the anticancer agent from the blood.

The anticancer agent is removed from the recovered blood or the like by blood cleaning treatment such as hemodialysis, hemofiltration, hemoabsorption or centrifugation using the blood cleaning device 40, as mentioned above, and is again sent back into the body as blood for transfusion.

It is also possible to subject the intracorporeal blood or the like after completion of the perfusion therapy to extracorporeal perfusion using the blood cleaning device 40, without administering any anticancer agent, to thereby eliminate the anticancer agent remaining in the body.

It is desirable that the settings display panel 77 be provided with a blood cleaning setting display (not shown) for enabling selection and setting for blood cleaning, namely selection as to whether the blood or the like discharged by the discharge pump 30 should be stored in the reservoir 39 or sent to a flow channel toward the blood cleaning device 40 for blood purification.

Thus, a constitution is possible such that when the blood cleaning selection setting is made by means of the blood cleaning setting display, the controller 33 transmits a signal to the three-way solenoid valves 74 to thereby direct the blood or the like to a predetermined route for cleaning. By doing so, it becomes possible to rapidly perform blood cleaning without exchanging or replacing the blood circuit, connecting tubes and so on.

It is also desirable that the settings display panel 77 be provided with a cancer therapeutic agent administration interval setting display (not shown) for enabling setting of the intervals of anticancer agent administration so that the anticancer agent can be fed automatically at the predetermined time intervals.

Thus, the system is constituted such that the controller 33 drives and controls the cancer therapeutic agent feeder 42 to feed the anticancer agent at the predetermined intervals as preset by means of the cancer therapeutic agent administration interval setting display. By this, it becomes possible to feed a predetermined amount of the anticancer agent into the body at constant intervals and thus precisely control the amount of the cancer therapeutic agent administered.

It is further desirable that the settings display panel 77 be provided with a cancer therapeutic agent concentration setting display (not shown) enabling setting of the anticancer agent concentration in the discharge so that the rate of discharge can be automatically adjusted so as to attain the predetermined anticancer agent concentration.

Thus, a constitution is possible such that a cancer therapeutic agent concentration sensor comprising a photosensor, a chemosensor or the like is used as the flow rate sensor 32-2 to thereby determine the concentration of the anticancer agent contained in the blood or the like discharged and that the fluid discharge rate is thus automatically adjusted by driving the constant flow valve 31-2 and the discharge pump 30 so that the predetermined amount of the anticancer agent-containing fluid may be discharged. By this, it becomes possible to precisely recover the anticancer agent remaining in the body.

A constitution is desirable such that the feeding pump 29 and discharge pump 30 each has a handle type clamp (not shown) and can be actuated manually. By this, it becomes possible to continue the perfusion safely even on the occasion of power failure or power source shutout.

Figure 8:
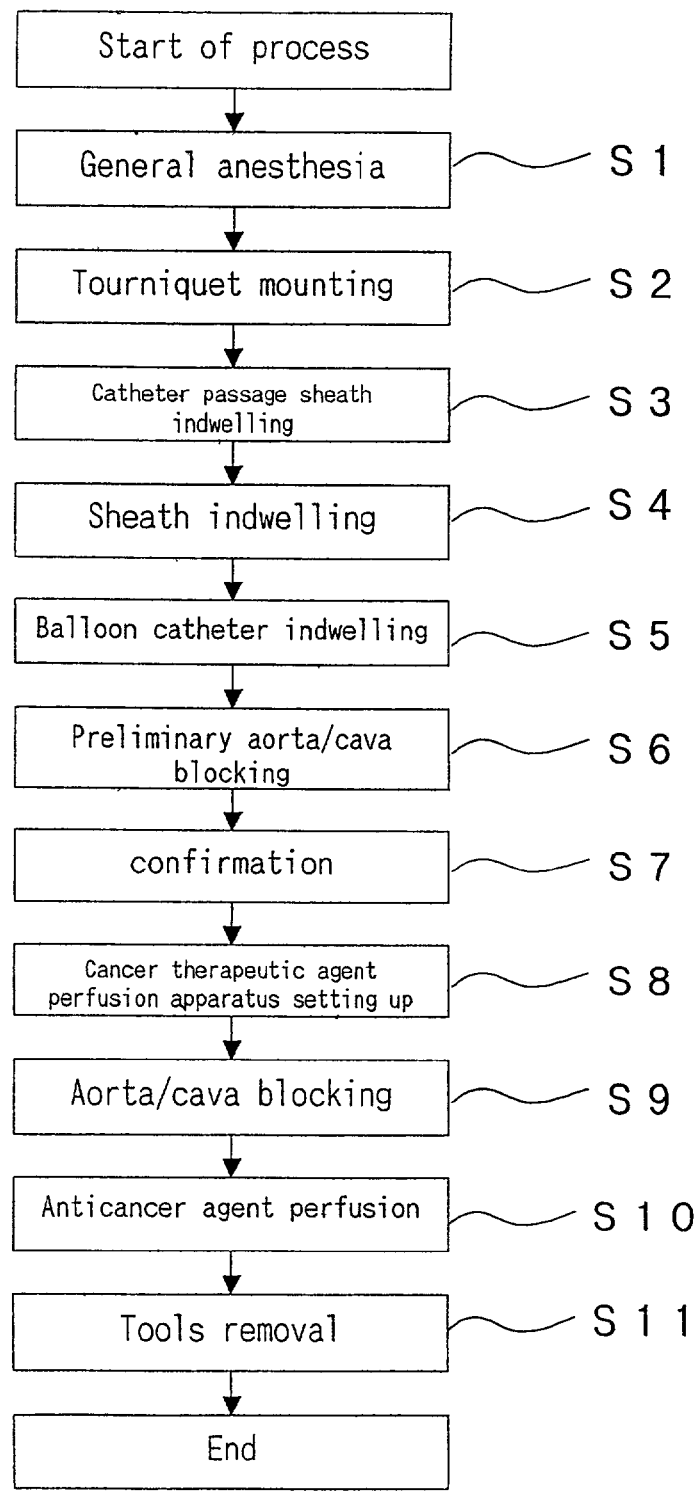
FIG. 8 is a flow chart illustrating the technique and procedure of the invention.

Now, referring to the block diagram shown in FIG. 8, the technique and procedure of the cancer therapeutic agent perfusion therapy, with using an anticancer agent as a cancer therapeutic agent, according to the invention is described. In the following procedure, it is presumed that the occurrence of advanced cancer in a site within the pelvis 59 is evident from at testing and that, based on the test results, no surgical operation is employed but perfusion therapy accompanying intervention alone is to be performed. The mode of embodiment is as shown in FIG. 1.

A patient 60 is generally anesthetized in the conventional manner (step S1).

Tourniquets 45 are mounted around the circumference of both femurs, as shown in FIG. 1 (step S2). Until the step of preliminary blocking of the aorta and cava in the step S6 to be mentioned later herein, the tourniquets 45 are kept in a loosened state so that the blood flow in the lower limbs may not be blocked.

As shown in FIG. 1, catheter passage sheaths 67 are indwelled in the aorta and cava in the conventional manner (step S3). Thus, the tip of a 9 Fr. catheter passage sheath 67-1 is percutaneously inserted into the right femoral artery 46 and indwelled in the right femoral artery 46. The tip of a 9 Fr. catheter passage sheath 67-2 is percutaneously inserted into the right femoral vein 47 and indwelled in the right femoral vein 47.

As shown in FIG. 1, sheaths 3 are indwelled in the aorta and cava in the conventional manner (step S4). Thus, the tip of a 6 Fr. sheath 3-1 is percutaneously inserted into the left femoral artery 52 and indwelled in the left femoral artery 52. Into the left femoral vein 53, there is percutaneously inserted the tip of a 5 Fr. sheath 3-2 and this is indwelled in the left femoral vein 53.

As shown in FIG. 1, a balloon catheter 48-1 is indwelled in the conventional manner under X ray fluoroscopy (step S5). Thus, the balloon catheter 48-1 is inserted into the right femoral artery 46 through the passage 63-1 for insertion and the balloon 49-1 is indwelled at a position just above the branching point 50 of the femoral artery. A balloon catheter 48-2 is inserted into the right femoral vein 47 through the passage 63-2 for insertion and the balloon 49-2 is indwelled at a position just above the common iliac confluence point 51 of the inferior vena cava.

In this embodiment, the balloon catheters 10 shown in FIG. 4 are used as the balloon catheters 48. The balloon catheter 48-1 has a size of 5 Fr. (30 mm in diameter) and the balloon catheter 48-2 has a size of 6 Fr. (40 mm in diameter).

In controlling the balloon catheters 48 under X ray fluoroscopy, syringes containing a contrast medium are connected to the three-way cocks 56 of the sheaths 3. Where there is a branching in the blood vessel, a radiopaque contrast medium is injected into the blood vessel by pressurizing the syringe and the balloon 49 is selectively advanced into the branching portion while performing angiography under X ray fluoroscopy.

In cases where the balloon catheters 16 according another embodiment of the present invention as shown in FIG. 5 are used as the balloon catheters 48 in lieu of the balloon catheters 10, it is not necessary to indwell the sheaths 3 in the right femoral artery and right femoral vein. Therefore, step S5 can be carried out directly after step S3, without using the sheaths 3 in step S4.

Preliminary cava blocking is carried out (step S6). Thus, the tourniquets 45 mounted in step S2 are inflated by pressurizing them to thereby block the blood flow in the lower limbs. Further, preliminary aorta/cava blocking is effected, between the tourniquets 45 and the balloons 49, by inflating the balloons 49 by pressurizing.

After preliminary cava blocking in step S6, the positions of collateral blood vessels (not shown) are confirmed (step S7). Thus, a radiopaque contrast medium is fed intravascularly and angiography is performed under X ray fluoroscopy and the sites and occurrence or nonoccurrence of collateral blood vessels in the regions of the above-mentioned preliminary aorta/cava blocking are checked and confirmed. After confirmation of the fact that collateral blood vessels to and from a cancer tissue or tissues 1 have been secured, hence the anticancer agent can reach the cancer tissue 1, the tourniquets 45 and balloons 49 are immediately deflated to thereby recover the blood flow.

The cancer therapeutic agent perfusion apparatus A 37 is set up as shown in FIG. 6 (step S8). Thus, a fluid feeding tube 27 is connected to the port A 54-1 provided at the rear end side of the sheath 3-1, and a fluid discharge tube 28 is connected to the port A 54-2 provided at the rear end side of the sheath 3-2. A syringe (not shown) containing necessary agents, for example an anticoagulant such as heparin and/or a contrast medium, is connected to the port B 55-1 provided at the three-way cock on the sheath 3-1.

Further, by means of the settings display panel 77 shown in FIG. 11, the "fluid feeding rate setting" displayed on the fluid feeding rate setting display 87 is set at "360 ml/min", the "fluid discharging rate setting" displayed on the fluid discharging rate setting display 88 at "380 ml/min", the "perfusion time setting" displayed on the perfusion time setting display 90 at "30 min" and the "cancer therapeutic agent feeding amount setting" displayed on the cancer therapeutic agent feeding amount setting display 91 at "200 ml".

The "fluid feeding rate setting" and "fluid discharging rate setting" can be made arbitrarily depending on the condition of the patient and other factors. It is, however, essential that the "fluid feeding rate setting" should be faster by at least 10 ml/min than the "fluid discharging rate setting". By determining the settings in the above manner, it becomes possible to lower the pressure on the discharge side as compared with the pressure on the feeding side in the system connecting the feeding side with the discharge side and thereby prevent the anticancer agent from leaking into blood flow routes occurring outside the pelvis 59 while maintaining the effects of the agent on the cancer tissue 1.

However, an excessive difference between the feeding rate and discharging rate results in an increase in blood transfusion although the leakage of the anticancer agent to the outside of the pelvis 59 decreases. Therefore, it is necessary to secure an appropriate difference therebetween.

Aorta/cava blocking is effected (step S9). Thus, while appropriately feeding an anticoagulant such as heparin, the tourniquets 45 are inflated by pressurizing at an appropriate pressure, to thereby block the blood flow in the lower limbs. The balloons 49 are also inflated by pressurizing at an appropriate pressure to thereby effect aorta/cava blocking between the tourniquets 45 and the balloons 49.

By actuating the operation switch 101 found on the settings display panel 77, anticancer agent perfusion is carried out (step S10). Thus, the anticancer agent is administered to the cancer tissue site 1 from the left femoral artery 52 via the aorta 57. That potion of the anticancer agent which has passed through the cancer tissue site 1 and into the cava 58 or that portion thereof which has passed through other collateral blood vessels than those leading to the cancer tissue site 1 and into the cava 58 is recovered, together with blood or the like, into the cancer therapeutic agent perfusion apparatus A 37 through the sheath 3-2.

During the above anticancer agent perfusion procedure, the cancer therapeutic agent administration key 102 is actuated at 10-minute intervals to thereby administer the anticancer agent to the cancer tissue site 1. The dose of the anticancer agent, the times of anticancer agent administration and the frequency of anticancer agent administration can be modified according to the patient's condition and based on the anticancer agent content in the blood as revealed by centrifugation of the blood stored in the reservoir 39 and/or urinalysis.

At an arbitrary but appropriate time, a haptoglobulin-containing antihemolytic agent may be administered intravenously.

It is desirable that during perfusion, the patient is induced to keep in such posture that does not inhibit the circulation of blood while blood transfusion or fluid transfusion is given.

After completion of the anticancer agent perfusion, the tourniquets 45 and balloons 49 are deflated and the aorta/cava blocking is removed. An appropriate amount of a heparin antagonist, such as protamine, is administered for the purpose of hemostasis.

It is also desirable that the fluid discharging tube 28 and feeding tube 27 (both sown in FIG. 6) be connected to a hemodialyzer (not shown) for depriving the blood or the like of the anticancer agent detained within the body. In cases where the cancer therapeutic agent perfusion apparatus B 38 is used in the cancer therapeutic agent perfusion therapy shown in FIG. 8, the blood or the like can be cleaned and the anticancer agent retained in the body can be eliminated by switching the channel in the three-way solenoid valve 74 over to the blood cleaner 40 side, without connecting the fluid discharging tube 28 and feeding tube 27 to a hemodialyzer (not shown).

After release from the aorta/cava blocking, the tools are removed (step S11). Thus, the sheaths 3, balloon catherters 48, introducers 2 and tourniquets 45 are removed and a hemostatic procedure is performed for preventing from bleeding. When the patient 60 is made to come out of anesthesia, the process is finished.

Meanwhile, the present inventors experimentally calculated the leakage of the cancer therapeutic agent fed by the cancer therapeutic agent perfusion therapy according to the invention into blood flow routes occurring outside the pelvis 59, based on the blood anticancer agent level as revealed upon blood specimen collection and the amount of the anticancer agent excreted into urine. A comparison, based on experiments, between the conventional cancer therapeutic agent perfusion therapy and the cancer therapeutic agent perfusion therapy according to the invention is shown below.

When the amount, per minute, of the body fluid containing the anticancer agent regionally injected into a tissue occurring in the pelvis is $\alpha$ [ml/min] and the amount, per minute, of the body fluid containing the anticancer agent aspirated from the same region is B [ml/min], the difference therebetween is given by (1) as follows:

$$(B-\alpha) = \lambda_{(B-\alpha)} \quad (1)$$

When, in equation (1), α[ml/min] is equal to B [ml/min], then $\lambda_0=0$ [ml/min].

The experiments carried out by the inventors revealed that the ratio γ of the loss of the anticancer agent (amount of the anticancer agent that had leaked into blood flow routes outside the pelvis, hence perfused through the whole body) to the amount injected was γ≈60% when the difference was $\lambda_0$. Thus, in the conventional cancer therapeutic agent perfusion therapy, 60% of the anticancer agent injected was circulated through the whole body.

On the contrary, in the cancer therapeutic agent perfusion therapy according to the present invention, γ=not more than 30% at $\lambda_{10}$, γ=15 to 20% at $\lambda_{20}$, γ=10 to 15% at $\lambda_{30}$, and γ=not more than 10% at $\lambda_{40}$.

Therefore, for attaining therapeutic effects by cancer therapeutic agent perfusion in the cancer therapeutic agent perfusion therapy according to the invention, it is necessary that the amount B of the body fluid containing the anticancer agent aspirated should be larger by at least 10 ml/min than the amount α of the body fluid containing the ant injected. By this, the amount of the anticancer agent perfused through the whole body can be suppressed to 30% or less of the amount injected.

Preferably, when the amount B of the body fluid containing the anticancer agent aspirated is larger by 20 to 30 ml/min than the amount α of the body fluid containing the anticancer agent injected, the anticancer agent perfused through the whole body can be suppressed to 10 to 20% of the amount injected, hence higher cancer chemotherapeutic effects can be obtained.

If, however, the amount B of the body fluid containing the anticancer agent aspirated is larger by more than 40 ml/min than the amount α of the body fluid containing the anticancer agent injected, blood transfusion may become necessary depending on the patient's condition although the amount of the anticancer agent perfused through the whole can be suppressed to 10% or less of the amount injected.

Therefore, it is necessary that the relation between the amount α of the body fluid containing the anticancer agent injected and the amount B of the body fluid containing the anticancer agent aspirated, namely (B−α)=x ,should satisfy the following relation (2):

$$\lambda_{10} \geq \lambda_x \geq \lambda_{40} (10 \leq x \leq 40) \quad (2)$$

When the relation (2) is satisfied, high cancer chemotherapeutic effects can be obtained while suppressing the adverse effects of the anticancer agent to the minimum.

EXAMPLE

An example of the present invention is now explained. Needless to say, the present invention does not limited to the example explained below.

Example 1

The intrapelvic perfusion therapy with cancer therapeutic agent of the present invention was carried out as explained below.

The present inventor calls the intrapelvic perfusion therapy with cancer therapeutic agent of the present invention NIPP (negative-balanced isolated pelvic perfusion), and the intrapelvic perfusion therapy with cancer therapeutic agent of prior art IPP (isolated pelvic perfusion).

The intrapelvic perfusion therapy with cancer therapeutic agent of the present invention was performed 21 times in patients having pelvic canser with the method described in preferred embodiments of the invention and FIG. 8.

Cisplatin, as an example of the anticancer agent, was dosed until the amount of platinum in cisplatin was included 200-300 mg. The blood including cisplatin is fed into the arteries at the flow rate of 300-360 [ml/min], and the blood including cisplatin is discharged from the veins at the flow rate of 320-385 [ml/min]. The perfusion was continued 30 minutes with keeping the difference between injection and aspiration flow rate was kept 20-25 [ml/min]. After performing this intrapelvic perfusion therapy, the blood of the intrapelvic circulation was dialyzed for 30 min.

As a result, the plasma pelvic to systemic exposure ratio during this intrapelvic perfusion was 14:1. And the percentage of drug leading from pelvic to systemic compartment during drug infusion (0 to 30 min.) was about 20%. These data was calculated by the known formula of Wanebo.

It is known that when the aspiration rate is set as same as the injection rate, plasma pelvic to systemic exposure ratio during the conventional intrapelvic perfusion is about 6:0, and that percentage of drug leading from pelvic to systemic compartment during drug infusion (0 to 10min.) with the conventional method is about 40% (Turk PS, Belliveau JF Darnowski J W, Weinberg M C, Leenen L, Wanebo H J, et al. Isolated pelvic perfusion for unresectable cancer using a balloon occlusion technique. Arch Surg. 128: 533-539. 1993; Wanebo H J Chung M D, Levy A I, Turk P S, Vezeridis M P, Belliveau J F. Preoperative therapy for advanced pelvic malignancy by isolated pelvic perfusion with the balloon occlusion technique. Ann Surg Oncol. 3; 295-303.1996; Wanebo H J, Belliveau J F. A pharmacokinetic model and clinical pharmacology of cis-platinum, 5-fluorouracil and mitomycin-C in isolated pelvic perfusion. Cancer Chemother & Pharmacol. 43: 427-434. 1999.).

Therefore, it is shown that plasma pelvic to systemic exposure ratio during the intrapelvic perfusion in this example is as twice as much as the ratio with the conventional method. The leakage of the cancer therapeutic agent into the systemic circulation can be successfully reduced and the concentration of the cancer therapeutic agent in the intrapelvic isolation can be kept higher than that of the prior art.

INDUSTRIAL APPLICABILITY

The present invention can produce the following effects.
(1) The cancer therapeutic agent can be inhibited from leaking into blood flow routes occurring outside the pelvis while maintaining the effects of administration thereof on the cancer tissue by recovering the blood or the like containing the cancer therapeutic agent from the vena cava in a larger amount as compared with the cancer therapeutic agent administered into the aorta so that the rate of discharging of the blood or the like containing the cancer therapeutic agent from the cava can be faster than the rate of feeding the cancer therapeutic agent fed into the aorta.
(2) The cancer therapeutic agent can be inhibited from being diffused through the whole body, hence the adverse effects of the cancer therapeutic agent can be reduced or prevented.
(3) The balloon catheter system by themselves make it possible to block the blood flow by inflated balloons and intracorporeally administer the agent and recover the same, so that the number of tools to be percutaneously inserted into the patient's body or blood vessels and indwelled therein can be reduced.
(4) When the cancer therapeutic agent perfusion apparatus A is used, the cancer therapeutic agent can be administered and recovered with certainty and precise dose and recovery control or management can be accomplished.
(5) The cancer therapeutic agent perfusion apparatus A makes it possible to preset the rate of recovery of the blood or the like at a higher level than the rate of feeding of the cancer therapeutic agent, so that the cancer therapeutic agent can be inhibited from leaking into blood flow routes outside the pelvis while the effects of dosing thereof on the cancer tissue can be maintained. Therefore, the cancer therapeutic agent can be prevented from being diffused throughout the whole body.

What is claimed is:

1. An intrapelvic cancer therapeutic agent perfusion method for therapy of a cancer tissue site occurring within the pelvis of a patient, said method comprising:
    percutaneously inserting a tip of a first sheath, which is a tubular body, into the femoral artery of the patient;
    percutaneously inserting a tip of a second sheath, which is a tubular body, into the femoral vein of the patient;
    percutaneously inserting a first balloon catheter, having an inflatable first balloon at the tip of a flexible tubular body, into a predetermined site within the aorta of the patient through the femoral artery;
    percutaneously inserting a second balloon catheter, having an inflatable second balloon at the tip of a flexible tubular body, into a predetermined site within the vena cava of the patient through the femoral vein;
    blocking the blood flow at a lower limb side arterial site, lower than the predetermined site within the aorta;
    blocking the blood flow at a lower limb side venous site, lower than the predetermined site within the vena cava;
    inflating the first balloon to thereby form an intraarterial closed region between the predetermined site within the aorta and the lower limb side arterial site;
    inflating the second balloon to thereby form an intravenous closed region between the predetermined site within the vena cava and the lower limb side venous site;
    administering a body fluid containing a cancer therapeutic agent to the intraarterial closed region, through the first sheath; and
    recovering a body fluid containing the cancer therapeutic agent from the intravenous closed region through the second sheath at a first rate, said first rate being 10 ml/min-40 ml/min greater than a second rate at which the body fluid containing the cancer therapeutic agent is administered through the first sheath.

2. An intrapelvic cancer therapeutic agent perfusion method as claimed in claim 1, wherein, in the administering of the body fluid containing the cancer therapeutic agent and in the recovering of the body fluid, an extracorporeal blood circulation device is used.

3. An intrapelvic cancer therapeutic agent perfusion method as claimed in claim 1, wherein the cancer therapeutic agent is at least one agent chosen from the group consisting of anticancer agents, radioisotopes, genes for gene therapy, DNA molecules for gene therapy, RNA molecules for gene therapy and cells for gene therapy.

4. An intrapelvic cancer therapeutic agent perfusion method as claimed in claim 1 further comprising:
    cleaning the recovered body fluid by subjecting the recovered body fluid to at least one treatment selected from the group consisting of hemodialysis, hemofiltration, hemoabsorption and centrifugation; and
    returning the treated body fluid back into the body through the first sheath.

5. An intrapelvic cancer therapeutic agent perfusion method as claimed in claim 1 wherein said first rate is 20 ml/min-30 ml/min greater than said second rate.

6. An intrapelvic cancer therapeutic agent perfusion method as claimed in claim 1 wherein said administering is by means of a fluid feeding pump with discharge through a feed control valve and said recovering is by means of a fluid discharge pump with intake through a discharge control valve, said method further comprising:
    controlling said first and second rates by use of a controller for controlling said pumps and said control valves.

7. An intrapelvic cancer therapeutic agent perfusion method as claimed in claim 6 further comprising:
    sensing said first and second rates using first and second flow rate sensors, respectively; and
    wherein said controller controls said pumps and control valves in a feedback manner in accordance with signals received from said flow rate sensors.

8. An intrapelvic cancer therapeutic agent perfusion method as claimed in claim 1, further comprising:
    sensing said first and second rates using first and second sensors, respectively; and
    displaying, on a common display, values based on signals from said first and second sensors.

9. An intrapelvic cancer therapeutic agent perfusion method for therapy of a cancer tissue site occurring within the pelvis of a patient, said method comprising:
    percutaneously inserting a first balloon catheter having a first inflatable balloon at a tip of a flexible tubular body, having a first tube connected to its rear end opposite the tip, into a predetermined site within the aorta through the femoral artery of the patient;
    inserting a second balloon catheter having a second inflatable balloon at a tip of a flexible tubular body, having a second tube connected to its rear end opposite the tip, to a predetermined site within the vena cava;
    blocking blood flow at a lower limb side arterial site, lower than the predetermined site within the aorta;
    blocking the blood flow at a lower limb side venous site, lower than the predetermined site within the vena cava;
    inflating the first balloon to thereby form an intraarterial closed region between the predetermined site within the aorta and the lower limb side arterial site;
    inflating the second balloon to thereby form an intravenous closed region between the predetermined site within the vena cava and the lower limb side venous site;
    administering a body fluid containing a cancer therapeutic agent into the intraarterial closed region through the first tube;
    recovering a body fluid containing the cancer therapeutic agent from the intravenous closed region through the second tube at a first rate, said first rate being 10ml/min-40 ml/min greater than a second rate at which the body fluid containing the cancer therapeutic agent is administered through the first tube.

10. An intrapelvic cancer therapeutic agent perfusion method as claimed in claim 9, wherein, in the administering of the body fluid containing the cancer therapeutic agent and in the recovering of the body fluid, an extracorporeal blood circulation device is used.

11. An intrapelvic cancer therapeutic agent perfusion method as claimed in claim 9, wherein the cancer therapeutic agent is at least one agent chosen from the group consisting of anticancer agents, radioisotopes, genes for gene therapy, DNA molecules for gene therapy, RNA molecules for gene therapy and cells for gene therapy.

12. An intrapelvic cancer therapeutic agent perfusion therapy as claimed in claim 9 further comprising:
   cleaning the recovered body fluid by subjecting the recovered body fluid to at least one treatment selected from the group consisting of hemodialysis, hemofiltration, hemoabsorption and centrifugation; and
   returning the thus-treated body fluid into the body through the first tube.

13. An intrapelvic cancer therapeutic agent perfusion method as claimed in claim 9 wherein said first rate is 20 ml/min-30 ml/min greater than said second rate.

14. An intrapelvic cancer therapeutic agent perfusion method as claimed in claim 9 wherein said administering is by means of a fluid feeding pump with discharge through a feed control valve and said recovering is by means of a fluid discharge pump with intake through a discharge control valve, said method further comprising:
   controlling said first and second rates by use of a controller for controlling said pumps and said control valves.

15. An intrapelvic cancer therapeutic agent perfusion method as claimed in claim 14 further comprising:
   sensing said first and second rates using first and second flow rate sensors, respectively; and
   wherein said controller controls said pumps and control valves in a feedback manner in accordance with signals received from said flow rate sensors.

16. An intrapelvic cancer therapeutic agent perfusion method as claimed in claim 9, further comprising:
   sensing said first and second rates using first and second sensors, respectively; and
   displaying, on a common display, values based on signals from said first and second sensors.

* * * * *